United States Patent [19]

Kelly et al.

[11] Patent Number: 5,541,339
[45] Date of Patent: Jul. 30, 1996

[54] CC-1065 ANALOGS HAVING TWO CPI SUBUNITS

[75] Inventors: Robert C. Kelly, Augusta; Paul A. Aristoff, Portage, both of Mich.

[73] Assignee: The Upjohn Company, Kalamazoo, Mich.

[21] Appl. No.: 659,415

[22] PCT Filed: Aug. 7, 1989

[86] PCT No.: PCT/US89/03329

§ 371 Date: Mar. 8, 1991

§ 102(e) Date: Mar. 8, 1991

[87] PCT Pub. No.: WO90/02746

PCT Pub. Date: Mar. 22, 1990

Related U.S. Application Data

[63] Continuation of Ser. No. 243,350, Sep. 12, 1988, abandoned.

[51] Int. Cl.⁶ .................................................. C07C 487/02
[52] U.S. Cl. ............................................ 548/421; 548/433
[58] Field of Search ...................... 548/421, 433

[56] References Cited

U.S. PATENT DOCUMENTS 4,169,888  10/1979  Hanka et al. ............................ 424/121
4,413,132  11/1983  Werenga et al. ......................... 548/433
4,912,227   3/1990  Kelly et al. ............................... 548/421

FOREIGN PATENT DOCUMENTS 0154445     9/1985  European Pat. Off. .
PCT/US87/
  03227    12/1987  WIPO .

OTHER PUBLICATIONS

Martin, D. G. et al, "CC–1065 Transformations", J. Antibiotics, 1985, vol. 38, pp. 746–752.

Wierenga, W., "Synthesis of the Left–Hand Segment of the Antitumor Agent CC–1065", J. Am. Chem. Soc. 103, No. 18, 1981, pp. 5621–5623.

Primary Examiner—Johann Richter
Assistant Examiner—Laura R. Cross
Attorney, Agent, or Firm—William G. Jameson

[57] ABSTRACT

This invention concerns chemical compounds of general Formula I $$CPI_1\text{-}R_5\text{-}T\text{-}R'_5\text{-}CPI_2 \qquad \qquad I$$

The compounds of Formula I are useful as uv light absorbers, antibacterial agents, and are particularly useful as antitumor agents. Representative compounds of Formula I have been shown to possess useful ranges of antitumor activity in standard laboratory animal tests.

10 Claims, No Drawings

CC-1065 ANALOGS HAVING TWO CPI SUBUNITS

CROSS REFERENCE TO RELATED APPLICATIONS

This application is the national phase of PCT/US89/03329, filed 7 Aug. 1989; which is a continuation of Ser. No. 07/243,350, filed 12 Sep. 1988, now abandoned.

BACKGROUND OF THE INVENTION

Antibiotic CC-1065, (7bR,8aS)-7-[[1,6-dihydro-4-hydroxy-5 -methoxy-7-[(4,5,8,8a-tetrahydro-7-methyl-4-oxocyclopropa[c]pyrrolo[3,2-e]indol-2(1H)-yl)carbonyl]benzo [1,2-b:4,3-b']dipyrrol-3(2H)-yl]carbonyl]1,6-dihydro-4-hydroxy-5-methoxy-benzo[1,2-b:4,3-b']dipyrrole- 3(2H)-carboxamide, is disclosed and claimed in L. J. Hanka et al. U.S. Pat. No. 4,169,888 together with a process for preparing antibiotic CC-1065 by aerobic fermentation procedures, and recovering antibiotic CC-1065 therefrom.

In The Journal of Antibiotics, 1985, 38, 746, D. G. Martin et al reported that acetic acid adds across the spirocyclopropylcyclohexadienyl (SCPCH) system of CC-1065 to produce the phenolic, acetic acid product (AAP), 7-[[7-[[1-[(acetyloxy)methyl]-1,6-dihydro-5-hydroxy-8-methylbenzo [1,2-b:4,3-b']dipyrrol-3(2H)-yl]carbonyl]-1,6-dihydro-4-hydroxy-5-methoxybenzo[1,2-b:4,3-b']-dipyrrol-3(2H)-yl] carbonyl]-1,6 -dihydro-4-hydroxy-5-methoxy-benzo[1,2-b:4,3-b']dipyrrole-3(2H)-carboxamide. AAP was tested in vitro and in vivo and found to be less potent than CC-1065 by a factor of $10^3$ to $10^4$ depending upon the particular test system and therefore tended to divert attention from adducts of the SCPCH system as useful antitumor agents or as prodrugs to CC-1065 analogs.

In J. Am. Chem. Soc., 103, No. 18, 1981, W. Wierenga published a "Synthesis of the Left-Hand Segment of the Antitumor Agent CC-1065".

EP Application 0 154 445 (published Nov. 9, 1985) discloses various analogs of antibiotic CC-1065, including compounds of formula EP-I and EP-II (see General Formula chart of EP 0154 445), wherein $R_1$ in formula EP-II is $CH_3$—, —$CH_2Ph$, $CH=CHCH_2$—, —$CH_2SCH_3$, —$CH_2OCH_3$, —$CH_2OCH_2CH_2OCH_3$, —$CH_2CCl_3$, —$CH_2CH_2Si(R_2)_3$, or H, where Ph is phenyl; R is alkyl($C_1$-$C_5$), phenyl, or H; $R_2'$ is $C_1$ to $C_5$-alkyl, phenyl or hydrogen, and is not necessarily the same as R in one compound; $R_3$ is alkyl($C_1$-$C_5$), phenyl, or H; and X is Cl, Br, I or $OSO_2R_{40}$, where $R_{40}$ is $C_1$ to $C_5$-alkyl, phenyl, tolyl, bromophenyl, nitrophenyl, or trifluromethyl. The O-protected compounds of formula EP-II are chemically stable and only removable under specific chemical conditions. However, when the compounds of formula EP-II are O-deprotected, they can be cyclized to yield the compounds of EP-I.

EP Application 0 154 445 also discloses CPI dimers joined by —CO—$(CH_2)_{n1}$—CO— where $n_1$ is 2–12 and CPI dimers joined by the tether —C(O)—(—$R_{11}$—)—C(O)—$X_7$—($CH_2CH_2$—$X_7$)n4—C(O)—(—$R_{11}$—)—C(O)— where $R_{11}$=$CH_2CH_2$, CH=CH; and $X_7$—O, NH, and n4=1–4, and the HCl and MeI salts for $X_7$=NH.

Additional dimers of CPI prodrugs joined by —CO—$(CH_2)_{n1}$—CO— where $n_1$ is 2–2 and CPI dimers Joined by the tether —C(O)—(—$R_{11}$—)—C(O)—$X_7$—(—$CH_2CH_2$—$X_7$)n4—C(O)—(—$R_{11}$)—C(O)— where $R_{11}$= $CH_2CH_2$, CH=CH; and $X_7$=O, NH, and n4=1–4, and the HCl and MeI salts for $X_7$=NH are disclosed in U.S. patent application Ser. No. 944,633, filed 19 Dec. 1986, now abandoned, and PCT/U.S. application Ser. No. 87/03227, filed 11 Dec. 1987, published 14 Jul. 1988.

Various oral and poster presentations of material in U.S. patent application Ser. No. 944,633, filed 19 Dec. 1986, have been made.

SUMMARY OF THE INVENTION

This invention provides some new synthetically obtained compounds of formula I (see General Formulae Chart), as defined hereinafter, which are useful as uv light absorber substances, or as chemical intermediates. Representative formula I compounds have also been shown to possess useful ranges of antitumor activity in standard laboratory animal tests. The compounds of this invention are obtained by chemical processes shown in Schemes 1–6 and detailed in the examples.

DETAILED DESCRIPTION OF THE INVENTION

More specifically, this invention provides new chemical compounds of general Formula I (see GENERAL FORMULA sheet)

wherein $CPI_1$ and $CPI_2$, being the same or different, are selected from Formula A or B (see GENERAL FORMULA sheet);

wherein W is selected from $C_1$-$C_5$ alkyl, phenyl or hydrogen;

wherein X is selected from azido, a halogen atom, cyanate, thiocyanate, isocyanate, thioisocyanate, phosphate diester (—O—PO(OR)$_2$), phosphonyl (—O—PO$_2$R), thiophosphonyl (—O—PSOR), sulfinyl (—O—SOR) or sulfonyl (—O—SO$_2$R);

wherein Y is selected from hydrogen, —C(O)R, —C(S)R, —C(O)OR$_1$, —S(O)$_2$R$_1$, —C(O)NR$_2$R$_3$, —C(S)NR$_2$R$_3$, or —C(O)NHSO$_2$R$_4$;

wherein Z is selected from the group consisting of $C_1$-$C_5$ alkyl, phenyl or hydrogen:

wherein R is selected from the group consisting of $C_1$-$C_{20}$ alkyl; $C_2$-$C_6$ alkenyl; $C_2$-$C_6$ alkynyl; phenyl optionally substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro; naphthyl optionally substituted with one or 2 $C_1$-$C_4$ alkyl, $C_1$-$C_3$ alkoxy, halo, triflurometyl, $C_2$-$C_6$ dialkylamino, $C_1$-$C_3$ alkylthio or nitro;

wherein $R_1$ is selected from $C_1$-$C_{20}$ alkyl or phenyl optionally substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro;

wherein $R_2$ and $R_3$, being the same or different, are selected from hydrogen, $C_1$-$C_{20}$ alkyl, or phenyl optionally substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro; with the proviso that both $R_2$ and $R_3$ can not be phenyl or substituted phenyl;

wherein $R_4$ is selected from $C_1$-$C_{10}$ alkyl; phenyl optionally substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro; naphthyl optionally substituted with one or 2 $C_1$-$C_4$ alkyl, $C_1$-$C_3$ alkoxy, halo, trifluoromethyl, $C_2$-$C_6$ dialkylamino, $C_1$-$C_3$ alkylthio or nitro;

wherein T is a tether linkage selected from the group consisting of:
a) aminocarbonyl (—NHC(O)—);
b) carbonylamino (—C(O)NH—);
c) carbonyloxy (—C(O)O—);
d) oxycarbonyl (—OC(O)—);
e) amino-tether-amino of the formula —NR$_{13}$—T'—NR$_{14}$— where R$_{13}$ and R$_{14}$, being the same or different, are hydrogen, or C$_1$–C$_8$ alkyl, or when taken together are —(CH$_2$)$_n$— where n is! 2 or 3; where T' is selected from the group consisting of carbonyl (—C(O)—), dicarbonyl (—C(O)C(O)—), (—C(O)(CH$_2$)$_n$C(O)—), where n is 1 to 5, (—C(O)PhC(O)—), where Ph is 1,3- or 1,4-phenylene, or a group of the formula —C(O)-het-C(O)—, where -het- is as defined below; or
f) —C(O)-het-C(O)—, when R$_5$ and R'$_5$ are both a direct bond, wherein -het- is a fused mono-, di-, or tricyclic heteroaryl of 5 to 12 members, containing one, two, or three heteroatoms selected from the group consisting of oxygen, nitrogen or sulfur, optionally substituted with one or 2 C$_1$–C$_4$ alkyl, C$_1$–C$_3$ alkoxy, halo, C$_1$–C$_3$ alkylthio, trifluoromethyl, C$_2$–C$_6$ dialkylamino, or nitro;

wherein R$_5$ and R'$_5$, being the same or different, are selected from a direct bond or a carbonyl acyl group selected from the group consisting of a compound of formula (ii), (vi), (viii), (x), (xi), (xvii), (xviia), (xviib), (xviii), (xix), (xx), (xxi), (xxii), (xxiii), (xxiv), (xxv), (xxvi) as defined in Chart C where the indicated free valence bonded to the carbonyl carbon atom is bonded to the indicated free valence of the nitrogen (N—) in CPI$_1$ or CPI$_2$ and the other indicated free valence represents a bond to the tether group T.

CPI$_1$ and CPI$_2$, being the same or different, are preferably 1-(chloromethyl)-1,6-dihydro-8-methyl-5-hydroxy-benzo[1,2-b:4,3-b']dipyrrole-3(2H)-yl or 4,5,8,8a-tetrahydro-7-methyl-4-oxocyclopropa[c]-pyrrolo(3,2-e)indol-2(1H)-yl.

W is preferably methyl.

X is preferably halogen, more preferably chloro or bromo.

Y is preferably —COR, wherein R is selected from C$_1$–C$_{10}$ alkyl; phenyl optionally substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro; —C(O)NHSO$_2$R$_4$; or —C(O)NR$_2$R$_3$.

Z is preferably hydrogen.

T is preferably an amide (aminocarbonyl); carbonylamino (—C(O)NH—); or an amino-tether-amino of the formula —NR$_{13}$—T'—NR$_{14}$— where R$_{13}$ and R$_{14}$ are hydrogen and where T' is selected from carbonyl (—C(O)—) or a group of the formula —C(O)-het-C(O)—, where -het- is a heteroaryl selected from Supplemental Formula Chart, especially preferred are pyrrol-2,5-diyl, fur-2,5-diyl, indol-2,5-diyl, benzofuran-2,5-diyl or 3,6-dihydrobenzo[1,2-b:4,3-b']dipyrrol-2,7-diyl. The indicated free valences of -het- are bonded to the carbonyl carbon atoms (—C(O)-het-C(O)—).

R$_5$ is preferably 2-carbonylindole-5-yl, 2-carbonyl-6-hydroxy-7-methoxyindol-5-yl, 2-carbonyl-1,2,3,6-tetrahydrobenzo[1,2-b:4,3b']dipyrrol-6-yl, 2-carbonyl-3-hydroxy-4-methoxy-1,2,3,6-tetrahydrobenzo[1,2-b:4,3-b']dipyrrol-6-yl.

Halogen atom (halo) refers to a bromo, chloro, iodo or fluoro atom.

Examples of C$_1$–C$_{20}$ alkyl are methyl, ethyl, propyl, butyl and the like, including isomeric forms thereof. Examples of C$_1$–C$_3$ alkoxy are methoxy, ethoxy, propoxy and isomeric forms thereof. Examples of C$_2$–C$_6$ dialkylamino are dimethylamino, diethylamino, methylethylamino, dipropylamino and ethylpropylamino. Examples of aminocarbonylalkyl-(C$_1$–C$_{10}$) are aminocarbonylpentyl (—NHCOC$_5$H$_{11}$) and aminocarbonylmethyl (—NHCOCH$_3$).

Examples of het include furan-2,4-diyl, furan-2,5-diyl, pyrrol-2,4-diyl, pyrrol-2,5-diyl, thiophen-2,4-diyl, thiophen-2,5-diyl, indol-2,5-diyl, benzofuran-2,5-diyl, benzothiophen-2,5-diyl, pyridin-2,6-diyl, pyrazin-2,6-diyl, pyrimidin-2,6-diyl, quinolin-2,6-diyl, quinoxalin-2,6-diyl, quinazolin-2,6-diyl, benzo[1,2-b:4,3-b']-dipyrrol-2,7-diyl, benzo[1,2-b:4,3-b']difuran-2,7-diyl, benzoxazol-2,5-diyl.

Examples of optionally substituted het are 3,4-dichlorofuran-2,5-diyl 3,4-dimethylfuran-2,5-diyl, 3-chloropyrrol-2,5-diyl, 3,4-dichloropyrrol-2,5-diyl, 3-methoxypyrol-2,5-diyl, 3-methyl-4-ethylpyrrol-2,5-diyl, 3,4-difluoropyrrol-2,5-diyl, 3-bromo-thiophen-2,5-diyl, 4-chloropyridin-2,6-diyl, 4,5-dimethoxybenzo[1,2-b:4,3-b']-dipyrrol-2,7-diyl, 3,5-dichloropyridin-2,6-diyl.

The compounds of formula B on the GENERAL FORMULA sheet can be named as derivatives of the numbering system (B') shown on the GENERAL FORMULA sheet. Such compounds will contain the 1,2,3,6-tetrahydro-8-W-5-Y-benzo[1,2-b:4,3-b']dipyrrol-1-[Z—CH(X)]-structure.

The compounds of Formula I are drawn as the racemic mixture and include the natural isomer of Formula I'a which can be resolved from the racemic mixture and/or prepared from starting materials of the natural, i.e. 1(S)-configuration.

Examples of Formula I compounds of this invention include:
[S-(R*,R*)]-6,6'-[carbonylbis(5-imino-1H-indole-2-carbonyl)]bis[8-chloromethyl)-3,6,7,8-tetrahydro-1-methylbenzo[1,2-b:4,3-b']dipyrrol-4-ol (Compound 1);
[7bR-[2(7'bR*, 8'aS*),7bR*,8aS*]]-2,2'-[carbonylbis(5-imino-1H-indole-2-carbonyl)]bis[1,2,8,8a-tetrahydro-7-methyl-cyclopropa(c)pyrrolo[3,2-e]indol-4(5H)-one (Compound 2);
(R*, S*)-N,N'-bis[2-[[1-(chloromethyl)-1,6-dihydro-5-hydroxy-8-methylbenzo[1,2-b:4,3-b']dipyrrol-3(2H)-yl]carbonyl]-1H-indol-5-yl]-ethanediamide (Compound 3);
[S-(R*,R*)]-6,6'-(1H-pyrrole-2,5-diyldicarbonyl)bis[8-(chloromethyl)-3,6,7,8-tertrahydro-1-methyl-benzo[1,2-b:4,3-b'-]dipyrrol-4-ol (Compound 4);
[S-(R*,R*)]-6,6'-(2,5-furandiyldicarbonyl)bis[8-(chloromethyl)-3,6,7,8-tetrahydro-1-methyl-benzo[1,2-b:4,3'b]dipyrrol-4-ol (Compound 5);
[S-(R*,R*]-N,N'-bis[2-[[1-(chloromethyl)-1,6-dihydro-5-hydroxy-8-methylbenzo[1,2-b:4,3-b']dipyrrol-3(2H)-yl]carbonyl]-1H-indol-5-yl]-2,5-furandicarboxamide (Compound 6);
[S-(R*,R*)]-N,N'-bis[2[[1-(chloromethyl)-1,6-dihydro-5-hydroxy-8-methylbenzo[1,2-b:4,3-b']dipyrrol-3(2H)-yl]carbonyl]-1H-indol-5-yl]-1H-pyrrole-2,5-dicarboxamide (Compound 7);
[R-(R*,S*)]-N,N=-bis[2-[[1-(chloromethyl)-1,6-dihydro-5-hydroxy-8-methylbenzo[1,2-b:4,3-b']dipyrrol-3(2H)-yl]carbonyl]-1H-indol-5-yl]-propanediamide (Compound 8);
[S-(R*,R*)]-6,6'-[carbonylbis(5imino-1H-indole-2-carbonyl)-bis[8-(chloromethyl)-3,6,7,8-tetrahydro-1-methyl-benzo[1,2-b:4,3'b]dipyrrol-4-ol diacetate (Compound 9);
[S-(R*, R*)]-6, 6'-(1H-indole-2,5-diyldicarbonyl)bis[8-(chloromethyl)-3,6,7,8-tetrahydro-1-methyl-benzo[1,2-b:4,3-b']dipyrrol-4-ol (Compound 10);
[S-(R*,R*)]-N,N'-bis[2-[[1-(chloromethyl)-1,6-dihydro-5-hydroxy-8-methylbenzo[1,2-b:4,3-b']dipyrrol-3(2H)-yl]carbonyl]-1H-indol-5-yl]-1H-indole-2,5-dicarboxamide (Compound 11);

[S-(R*,R*)]-2-[[1-(chloromethyl)-1,6-dihydro-5-hydroxy-8-methyl-benzo[1,2-b:4,3-b']dipyrrol-3(2H) -yl]carbonyl]-N-[2-[[1-(chloromethyl)- 1,6-dihydro-5-hydroxy-8-methylbenzo[1,2-b:4,3-b']dipyrrol( 3(2H) -yl]carbonyl]-1H-indol-5-yl]-1H-indole-5-carboxamide (Compound 12);

[S-(R*,R*)]-5-[[1-(chloromethyl)-1,6-dihydro-5-hydroxy-8 -methylbenzo[1,2-b:4,3- b']dipyrrol-3(2H)-yl]-carbonyl)-N-[2-[[1 -(chloromethyl)-1,6-dihydro-5-hydroxy-8-methylbenzo[1,2-b:4,3-b']dipyrrol- 3(2H) -yl]carbonyl) -1H-indol-5-yl]-1H-indole-2-carboxamide (Compound 13);

[S-(R*,R*)]-carbonylbis[imino-1H-indole-5,2-diylcarbonyl [1-(chloromethyl)- 1,6-dihydro-8-methylbenzo[1,2- b:4, 3-b']dipyrrole- 3,5(2H) -diyl]]ester, 2,2-dimethylpropanoic acid (Compound 14);

[S -(R*,R*)]-carbonylbis[imino-1H-indole-5,2-diylcarbonyl[1 -(chloromethyl)-1,6-dihydro-8-methylbenzo[1,2-b:4,3-b']dipyrrole- 3,5(2H)-diyl]]ester, decanoic acid (Compound 15);

[S-(R*,R*)]-6,6'-[carbonylbis[(7,8-dihydrobenzo[1,2-b:4,3 -b']dipyrrole-6,2(3H)-diyl)carbonyl]]bis[8-(chloromethyl)-3,6,7,8 -tetrahydro-1-methyl-benzo[1,2-b:4,3b'] dipyrrol-4-ol (Compound 16).

The compounds of Formula I are readily prepared by reacting the appropriate 4,5,8,8a-tetrahydro-4-oxocyclopropan(c)pyrrolo(3,2-e)indole analog (Formula B) with the biscarboxylic acid, bisisocyanate, bis-amino carboxylate or oxycarboxylate reagent and then with the other appropriate 4,5,8,8a-tetrahydro-4-oxocyclopropan(c)pyrrolo(3,2-e)indole analog (Formula B) as illustrated in Scheme 1, 2, 2a, 3, 4, 5 and 6 using the following reaction conditions:

Steps 1 and 4: Run in solution of 1 mg to 100 mg/ml in solvents such as ethyl acetate, methylene chloride or 1,2-dichloroethane with a gaseous acid at 1 to 5M such as HCl, or HBr or a strong organic acid such as $CF_3CO_2H$. The reaction run at 0° to 50° C. The product as an amine salt isolated by evaporation of solvent and acid. The reaction may be run from 10 min to 48 hr.

Step 2: Reaction run in polar solvent such as DMF, DMA, or THF at –10° to 50° C. Ratio of CPI moiety: biscarboxylic acid:dehydrating agent preferably 2:1:2. Dehydrating or coupling reagent can be a carbodiimide such as dicyclohexylcarbodiimide (DCC) or ethyldimethylaminopropylcarbodiimide (EDC) or other amide dehydrating agents known in the art. The reaction may be run from 10 min to 72 hrs.

Steps 5 and 7: Same as Step 2 but ratio of CPI moiety::acid:dehydrating reagent is preferably 1:1:1.

Steps 3, 8, 9, 11, 14, 15 and 17: The reaction is run in aqueous organic base. The preferred conditions are acetonitrile:water:triethylamine in a ratio of 1:1:1. The ratio of these reagents may change to 1:2:2 to 5:1:1. Also the solvents may change so that in place of acetonitrile may be used DMF, DMA, N-methylpyrrolidone, THF, etc. Also the organic base can be varied to other tertiary organic amines such as 1,5 diaza-bicyclo[3.3.3]octane (DABCO), or ethyl diisopropylamine. The temperature is usually 0° C. to 50° C. and the reaction is usually run for 5 min to 10 hr.

Step 6: The deprotection depends on the protecting group R. If it is t-butyl then the group may be removed by acid treatment similar to Step 1. If R=benzyl it may be removed by hydrogenolysis with Pd catalysis in ethyl acetate or THF, for example, or by ammonium formate, methanol, water and Pd/C. If $R=SiR_3$ then it may be removed by acid or fluoride ions. These methods are all well known in the art.

Steps 5a and 7a: The reactions may be run in aprotic polar solvents. Preferable are pyridine, DMF, DMA, THF, or methylene chloride. When the solvent is other than pyridine a base such as triethylamine may be added. The reaction is run in a ratio of CPI moiety to activated carbonyl compound of about 1:1. The reaction may be run at –50° to 100° C. and for from 5 min to 72 hr.

Steps 10 and 16: The reagents are combined in a ratio of CPI moiety to active carbonyl of about 2:1. The reaction may be run in polar aprotic solvents such as THF, DMF, DMA, pyridine, acetonitrile, etc. The reaction may be run at –50° C. to 100° C. and for 10 min to several weeks.

Steps 12, 13, 18 and 19: Ratio of CPI moiety to active carbonyl moiety of about 1:1. Otherwise run as Step 10.

In the following examples NMR spectral data were recorded in DMSO-d6 unless otherwise noted. IR spectra were recorded from Nujol mulls. Solutions for UV spectra were prepared by dissolving the solid in a few drops of DMF or dimethylacetamide (DMA) and diluting with 95% ethanol or methanol unless stated otherwise. TLC data is given for Analtech Uniplates of silica gel GF.

EXAMPLE 1

Preparation of [S-(R*,R*)]-6,6'-[carbonylbis(5-imino-1 H-indole-2-carbonyl)]bis[8-chloromethyl)-3,6,7,8-tetrahydro-1-methyl-benzo[1,2-b:4,3-b']dipyrrol-4-ol (Compound 1)

Part A-Preparation of 5,5'-(carbonyldiimino)bis-1H-indole-2-carboxylic acid diethyl ester.

A solution of 5-aminoindole-2-carboxylic acid ethyl ester (6.82 g, 33.4 mM) and 4-dimethylaminopyridine (19 mg, 0.15 mM) dissolved in THF (80 mL) are cooled to –98° C. in a frozen methanol bath. To this is added diisopropylethylamine (7 mL, 40.2 mM) followed by 1.93M phosgene in toluene (8.5 mL, 16.4 mM). The reaction is stirred at –98° C. for 1 hour, then at –78° C. for 1 hour. It is then stored at –13° C. overnight. The reaction is then quenched with water, and diluted with water and ethyl acetate. The aqueous layer is separated and re-extracted twice with ethyl acetate. The combined ethyl acetate layers are washed with N HCl, giving a mixture which is separated by filtration. The filtered solid is found to be pure product 5,5'-(carbonyldiimino)bis-1H-indole-2-carboxylic acid diethyl ester (6.38 g, 88%). The filtrate is dried and concentrated leaving 1.49 g of dark solid. This material is chromatographed over silica gel (100 g) eluted with 10% DMF in toluene. Twenty ml fractions are collected. Product is found by TLC in fractions 23–50. Concentration of these fractions under high vacuum leaves a residue which is crystallized from DMF-methanol. There is thus obtained an additional 0.80 g of product.

NMR: δ 1.36(t, 6H); 4.35(q, 4H); 7.10(s, 2H); 7.26(d, 2H, J=9 Hz); 7.39(d, 2H, J=9 Hz); 7.88(s, 2H); 8.52(s, 2H); 11.77(bs, 2H). IR: 3330, 3260, 1705, 1695, 1545, 1250 cm$^{-1}$ UV: $\lambda$max (THF)=338 nm ($\epsilon$=7000); 301 nm ($\epsilon$=28000); 292 nm ($\epsilon$=26000); 250 nm ($\epsilon$=31000). MS(FAB) m/z 435(M+ H), 406, 362, 253, 204, 159, 132. TLC: $R_f$=0.30 in (10-90) DMF-toluene.

Part B-Preparation of 5,5'-(carbonyldiimino)bis-1H-indole-2-carboxylic acid.

The indole dimer diester, 5,5'-(carbonyldiimino)bis-1H-indole-2-carboxylic acid diethyl ester, (7.16 g, 16.5 mM) is treated with pyridine (300 ml) and N NaOH (60 mL). The resultant mixture is stirred 24 hrs at 25° C., 7 hrs at 50°–60°

C., and additional 48 hrs at 25° C. at which point TLC indicates The reaction to be done. The reaction is concentrated at 25° C. under high vacuum to near dryness. The residue is acidified with 3N HCl and the resulting solid collected by filtration. The filtered solid is dissolved in DMF (100 ml) at about 100° C. The solution is then diluted with methanol (400 ml) and water (10 ml). The solution is cooled and the crystalline product 5,5'-(carbonyldiimino)bis-1H-indole-2-carboxylic acid is collected by filtration (5.11 g, 82%).

NMR: ε 7.07(d, 2H, J=2 Hz); 7.28(dd, 2H, J=1.8 Hz, J=9 Hz); 7.40(d, 2H, J=9 Hz); 7.89(d, 2H, J=1.8 Hz); 8.59(bs, 2HO); 11.65(d, 2H, J=1.5 Hz). IR: 3400–2300, 1680, 1530, 1225 cm$^{-1}$. UV: $\lambda$max=294 nm (ε=23000). MS(FAB): m/z 379(M+H), 362, 331, 253, 176, 158, 132. TLC: $R_f$=0.33 in (40-60-2) DMF-toluene-acetic acid.

Part C-Reaction of (S)-1-(chloromethyl)-1,6-dihydro-5-hydroxy- 8-methyl-benzo[1,2-b:4,3-b']dipyrrole-3(2H)-carboxylic acid 1,1-dimethyl ester [(Boc)CPI phenol chloride] with hydrogen chloride followed by condensation with 5,5'-(carbonyldiimino)bis-1H-indole-2-carboxylic acid.

(S)-1-(chloromethyl)-1,6-dihydro-5-hydroxy-8-methyl-benzo[1,2-b: 4,3-b']dipyrrole-3(2H)-carboxylic acid 1,1-dimethyl ester [(Boc)CPI phenol chloride] (128 mg, 0.38 mM) is dissolved in ethyl acetate (6 ml) and the solution treated with a freshly prepared solution of saturated HCl in ethyl acetate (6 ml). The reaction is stirred one hr at which time TLC shows the complete disappearance of starting material. The reaction solution is concentrated under vacuum and returned to atmospheric pressure under nitrogen. The resulting residue is twice re-evaporated from methylene chloride to give (S)-1 -(chloromethyl)-5-hydroxy-8-methyl-1,2,3,6-tetrahydro-benzo[1,2-b:4,3-b'] dipyrrole hydrochloride (CPI phenol chloride hydrochloride salt). This material is treated with a solution of the diacid, 5,5'-(carbonyldiimino)bis- 1H-indole-2-carboxylic acid, (78 mg, 0.21 mM) in of dry dimethylacetamide (4 ml). 1-Ethyl-3-(3-dimethylaminopropyl) carbodiimide hydrochloride (EDC, 68 mg, 0.08 mM) is then added as a solid. After 45 min, a second quantity of EDC is added (68 mg). Stirring is continued 50 min. The reaction is precipitated with water and the solid centrifuged. It is washed with 0.1 NHCl, 0.5% NaHCO$_3$ and water, centrifuging and withdrawing the aqueous each time. The residue is evaporated in vacuo at less than 20 torr over two days. The crude product is adsorbed from DMF onto Celite and chromatographed on a silica gel column (15 g) eluting with 30% DMF in toluene. Fractions of 10 ml are collected. [S-(R,,R*)]-6,6'-[carbonylbis(5-imino-1H-indole-2-carbonyl)]bis[8-chloromethyl)-3,6,7,8 -tetrahydro-1-methyl-benzo[1,2-b:4,3-b']dipyrrol-4-ol is found in fractions 4–16 (115.1 mg of solid, 74% yield based on BocCPI). NMR, IR, UV, FAB.

NMR: δ 2.356(S,6H); 3.582(m, 2H); 3.92(m, 2H); 4.03 (m, 2H); 4.548(m, 2H); 4.67(m, 2H); 7.044(s, 4H); 7.26(d, 2H); 7.42(d, 2H); 7.64(bs, 2H); 7.849(s, 2H); 8.466(bs, 2H); 9.767(bs, 2H); 10.704(bs, 2H); 11.531(bs, 2H). IR: 3260, 1580, 1195, cm$^{-1}$. UV: $^+$max=349 nm(ε=25000); 295 nm(ε= 31000). MS(FAB): m/z 815(M+H), 779, 579, 236, 201, 187, 159. DNA BINDING:

$\Delta[\Phi]_\lambda^{24h} \sim 0$

TLC: $R_f$=0.44 in (30-70)DMF-toluene.

EXAMPLE 2

Preparation of [7bR-[2(7'bR*,8'aS*),7bR*,8aS*]]-2, 2'-[carbonylbis(imino-1H-indole-5,2-dicarbonyl)]bis [1,2, -8,8a-tetrahydro-7-methyl-cyclopropa(c)-pyrrolo[3,2 -e]indol-4(5H)-one (Compound 2)

[S-(R*,R*)]-6,6'-[carbonylbis(8imino-1H-indole-2-carbonyl)]bis[8-chloromethyl)-3,6,7,8-tetrahydro-1-methyl-benzo[1,2-b:4,3-b']dipyrrol-4-ol (80 mg, 0.1 mM) is treated with acetonitrile (10 mL), water (3 mL) and triethylamine (3 mL). The reaction is stirred under nitrogen at room temperature. After 40 minutes the product which has precipitated is collected by filtration. The filtrate is diluted with water and ethyl acetate and a second quantity of product collected by filtration. The solids are combined giving [7bR-[2(7'bR*, 8'aS*),7bR*,*aS*]]-2,2'[carbonylbis(5-imino-1H-indole-2-carbonyl)]bis[1,2,8,8a-tetrahydro-7-methyl-cyclopropan(c)pyrrolo[3,2-e]indol- 4(5H)-one (38 mg, 52%).

NMR: ε 1.394(m, 2H); 2.008(s+m, 8H); 3.169(m, 2H); 4.44(m, 2H); 4.522(m, 2H); 6.693(s, 2H); 6.881(s, 2H); 7.120(s, 2H); 7.266(d, 2H); 7.402(d, 2H); 7.872(s, 2H); 8.512(bs, 2H); 11.536(bs, 2H); 11.675(bs, 2H). IR: 3250, 1560, 1375, 1255 cm$^{-1}$. UV: $\lambda$max=365 nm (ε-36000); 316 nm(ε=31000). MS(FAB): Calc'd. for $C_{43}H_{35}N_8O_5$:743.2730; found 743.2737. Ions at m/z 543, 368,201. DNA BINDING:

$\Delta[\Phi]_\lambda^{24h} \sim 0$

TLC: $R_f$=0.43 in (30-70) DMF-toluene.

EXAMPLE 3

Preparation of (R*,S*)-N,N'-bis[2-[[1-(chloromethyl)-1,6-dihydro-5-hydroxy-8-methylbenzo[1,2-b:4,3 -b']dipyrrol-3(2H)-yl]carbonyl]-1H-indol-5-yl]-ethanediamide (Compound 3)

Part A-Preparation of 5,5'-[(1,2-dioxo-1,2-ethanediyl)diimino]bis-1H-indole-2-carboxylic acid diethyl ester.

5-Aminoindole-2-carboxylic acid ethyl ester (190.4 mg, 0.93 mM) is dissolved in distilled THF (15 mL) under a nitrogen atmosphere, and the solution cooled to −78° C. Diisopropylethylamine (175 μl, 1.00 mM) is syringed in, followed by oxalyl chloride (41 μL, 0.47 mM). The reaction is stirred at −78° C. for one hr. The reaction is evaporated to half volume in vacuo, then treated with water. The product, 5,5'-[(1,2-dioxo-1,2-ethanediyl)diimino]bis-1H-indole-2-carboxylic acid diethyl ester, precipitates as a white solid which is collected by centifugation and dried 72 hrs at less than 20 torr (232 mg).

NMR: δ 1.348(t, 6H); 4.35(q, 4H); 7.16(s, 2H); 7.45(d, 2H); 7.68(d, 2H); 8.224(s, 2H); 10.732(bs, 2H); 11.92(bs, 2H). IR: 3360, 3320, 1690, 1670, 1525, 1255, 1215 cm$^{-1}$. UV: $\lambda$max=330 nm (ε=5000); 299 nm (ε=10000); MS(E1): m/z 462(M+), 417, 230, 204, 158.

Part B-Preparation of 5,5'-[(1,2-dioxo-1,2-ethanediyl)diimino]bis-1H-indole-2-carboxylic acid.

5,5'-[(1,2-dioxo-1,2-ethanediyl)diimino]bis-1H-indole-2-carboxylic acid diethyl ester (220 mg, 0.48 mM) is suspended in pyridine (9 mL) and treated with 1N NaOH (1.5 mL). The milky mixture is heated to 60° C. under nitrogen. After 24 hrs N NaOH again added (1 mL) and the reaction heated another 3 hrs. The reaction is then neutralized by the addition of 1N HCl (2.5 mL) and concentrated to one-half volume at less than 20 torr. The residue is then treated with 1N HCl (50 mL) and centrifuged giving a residual slightly pink solid. This is is washed with water, centrifuged, and dried in the vacuum oven leaving the product 5,5'-[(1,2-dioxo-1,2-ethanediyl)diimino]bis-1H-indole-2-carboxylic acid (148 mg).

NMR: κ 7.098(s, 2H); 7.42(d, 2H, J=9 Hz); 7.66(d, 2H, J=9 Hz); 8.201(s, 2H); 10.709(bs, 2H); 11.80(bs, 2H). IR: 3420, 3310, 1660, 1510, 1220 cm$^{-1}$. MS(FAB): m/z 407(M+H), 385, 331, 253, 177. TLC: R$_f$=0.31 in (40-60-2) DMF-Toluene-acetic acid.

Part C-Reaction of 5,5'-[(1,2-dioxo-1,2-ethanediyl)diimino]bis-1H-indole-2-carboxylic acid with (S)-1-(chloromethyl)-1,6 -dihydro-5-hydroxy-8-methyl-benzo[1,2-b:4,3-b']dipyrrole-3(2H)carboxylic acid 1,1-dimethyl ester [(Boc)CPI phenol chloride].

(S)-1-(chloromethyl)-1,6-dihydro-5-hydroxy-8-methyl-benzo[1,2 -b:4,3-b']dipyrrole-3(2H)-carboxylic acid 1,1-dimethyl ester [(Boc)CPI phenol chloride] (42.5 mg, 0.13 mM) is dissolved in ethyl acetate (1 mL) under a nitrogen atmosphere in the dark. The reaction is treated with ethyl acetate (3 mL) saturated with HCl. The reaction is stirred 1 hr and evaporated in vacuo. Nitrogen is let in when the vacuum is released. (S)-1-(chloromethyl)-5-hydroxy-8-methyl-1,2,3,6 -tetrahydro-benzo[1,2-b:4,3-b']dipyrrole hydrochloride (CPI phenol chloride hydrochloride) as a solid is obtained on re-evaporation 2× with CH$_2$C;$_2$. A suspension of 5,5'-[(1,2-dioxo-1,2-ethanediyl)diimino]bis-1H-indole-2-carboxylic acid (28.4 mg, 0.06 mM) in dimethylacetamide (2 mL) is added to the reaction. EDC is added as a solid (43.4 mg, 0.23 mM). The reaction is stirred in the dark under nitrogen at room temperature for 100 min. Water is added to precipitate the product. The solid, isolated by centrifugation, is washed twice with 5% NaHCO$_3$, then with 0.1N HCl and water. The solid is dried under vacuum. The solid is adsorbed from DMF onto silica gel, and chromatographed on a silica gel column (3 g) in 20% to 30% DMF in toluene. Fractions of 1–2 mL are collected. (R*,S*)-N,N'-bis[2-[[1 -(chloromethyl)-1,6-dihydro-5-hydroxy-8-methylbenzo[1, 2-[b:4,3b']dipyrrol-3(2H)-yl]carbonyl]-1H-indol-5-yl]-ethanediamide is found in fractions 15–22 (24.6 mg, 45% yield).

NMR: (DMF-d7) δ 2.216(s, 6H); 3.47(m, 2H); 3.77(m, 2H); 3.918(m, 2H); 4.51(m, 4H); 6.95(s, 2H); 7.03(s, 2H); 7.40(d, 2H); 7.62(d, 2H); 8.22(s,2H). UV: $\lambda$max=341 nm (ε=38000); 293 nm (ε=52000). TLC: R$_f$=0.58 in (30-70) DMF-toluene.

EXAMPLE 4

Preparation of [S-(R*,R*)]-6,6'-(1H-pyrrole-2,5-diyldicarbonyl)bis[8-(chloromethyl)-3,6,7,8-benzo [1,2-b:4,3-b']dipyrrol-4-ol (Compound 4)

(S)-1-(chloromethyl)-1,6-dihydro-5-hydroxy-8-methyl-benzo[1,2-b: 4,3-b']dipyrrole-3(2H)-carboxylic acid 1,1-dimethyl ester [(Boc)CPI phenol chloride] (40 mg, 0.12 nM) is dissolved in ethyl acetate (1 mL) under a nitrogen atmosphere. The reaction is treated with ethyl acetate freshly saturated with HCl (3 ml) and the resultant solution stirred at room temperature for 1 hr. The solvent is removed in vacuo, and the (S)-1-(chloromethyl)-5-hydroxy-8-methyl-1, 2,3,6-tetra-hydro-benzo[1,2-b:4,3-b']dipyrrole hydrochloride (CPI phenol chloride hydrochloride) as a purplish residual solid is re-evaporated 2× with CH$_2$CL$_2$, flushing with nitrogen between evaporations. This is treated with pyrrole-2,5-dicarboxylic acid (8.9 mg, 0.057 mM) in dry dimethylacetamide (1 mL) and EDC (24 mg, 0.125 mM) and the resultant solution stirred at 25 C. After 50 min. and additional quantity of EDC is added (24 mg, 0.125 mM). After an additonal 55 min the reaction is diluted with water (5 mL) and saturated aqueous sodium chloride solution (5 mL) and extracted with ethyl acetate 4 times. The combined organic layers are dried (Na$_2$SO$_4$) and evaporated. The crude residue is adsorbed from ethyl acetate-acetone onto 0.5 g silica gel and chromatographed on a 6 g silica gel column in 10% DMF-toluene followed by 15% DMF-toluene. Fractions of 3–4 ml are collected. [S(R*,R*)]-6,6'-(1H-pyrrole-2,5-diyldicarbonyl)bis[8-(chloromethyl)- 3,6,7,8-benzo[1,2-b:4,3-b']-]dipyrrol-4-ol is found in Fr. 23–37 (25 mg).

NMR: δ 2.349(s, 6H); 3.59(m, 2H); 3.90(m, 2H); 4.01(m, 2H); 4.40(m, 2H); 4.55(m, 2H); 6.850(s, 2H); 7.039(m, 2H); 7.60(m, 2H); 9.77(s, 2H); 10.71(bs, 2H);11.36(bs, 1H). UV: $\lambda$max=356 nm (ε=16000); 290 nm (ε=21000). TLC: R$_f$=0.47 in (20-80) DMF-toluene.

EXAMPLE 5

Preparation of [S-(R*,R*)]-6,6'-(2,5-furandiyldicarbonyl)bis[8-(chloromethyl)-3,6,7,8-tetrahydro-1-methyl-benzo[1,2-b 4,3-b']dipyrrol-4-ol (Compound 5).

(S)-1-(chloromethyl)-1,6-dihydro-5-hydroxy-8-methyl-benzo[1,2-b: 4,3-b']dipyrrole-3(2H)-carboxylic acid 1,1-dimethyl ester [(Boc)CPI phenol chloride] (40.6 mg, 0.12 mM) is dissolved in ethyl acetate (1 mL), put under nitrogen, and treated with HCl-saturated ethyl acetate (3 mL). After 50 minutes, the reaction is evaporated in vacuo, returning to atmospheric pressure under nitrogen. (S)-1-(chloromethyl)-5-hydroxy-8-methyl-1,2,3,6-tetrahydro-benzo[1,2-b:4,3-b'] dipyrrole hydrochloride (CPI phenol chloride hydrochloride) as a solid is obtained on re-evaporation 2× from CH$_2$Cl$_2$. The solid is treated with a solution of furan-2,5-dicarboxylic acid (9.7 mg, 0.062 mM) in dry dimethyl acetamide (1 mL). EDC (43.1 mg 0.22 mM) is added as a solid in 2 equal portions, 45 min apart. The reaction is stopped 170 min after the second addition, by adding ethyl acetate and water. The water is re-extracted with ethyl acetate. The combined organic layers are washed with 0.5N HCl, 1% NaHCO$_3$, and water. Drying (Na$_2$SO$_4$) and concentration gives a yellow solid (55.2 mg). The solid is adsorbed from DMF-acetone onto silica gel (0.7 g). This is placed on a silica gel column (7 g), eluting with 10% to 15% DMF in toluene. Fractions of 3–4 mL are collected. [S-(R*, R*)]-6,6'-(2,5-furandiyl-dicarbonyl)bis[8-(chloromethyl)-3, 6,7,8-tetrahydro-1-methyl-benzo[1,2-b 4,3-b']dipyrrol-4-ol, as a bright yellow solid, is isolated by concentrating fractions 23–31 (22.3 mg, 63% yield).

NMR: δ 2.344(s, 6H); 3.63(m, 2H); 3.89(m, 2H); 4.029(m, 2H); 4.51(m, 2H); 4.60(m, 2H); 7.048(s, 2H); 7.37(s, 2H); 7.64(m, 2H); 9.82(s, 2H); 10.75(bs, 2H). UV: $\lambda$max=360 nm (ε=20000); 295 nm (ε=24000). TLC: R$_f$=0.47 in (20-80) DMF-toluene.

EXAMPLE 6

Preparation of [S-(R*,R*]-N,N'-bis[2-[[1-(chloro-methyl)-1,6-dihydro-5-hydroxy-8-methylbenzo[1,2-b:4,3-b']dipyrrol-3(2H)-yl]carbonyl]-1H-indol-5-yl]-2,5-furandicarboxamide (Compound 6)

Part A-Preparation of 5,5'-[2,5-furandiylbis(carbonylimino)]-bis-1H-indole-2-carboxylic acid diethyl ester.

Furan-2,5-dicarboxylic acid (50 mg, 0.32 mM, A Sohst and B. Tollens, *Justig Liebigs Ann. Chem.*, 245, 1 (1888)) and 5-amino-indole- 2-carboxylic acid ethyl ester (130 mg, 0.64 mM) are dissolved in dimethylacetamide (2 mL) and the solution treated with EDC (132 mg, 0.69 mM). After 20 hrs the reaction is diluted with water (20 mL) and extracted twice with ethyl acetate. The combined ethyl acetate solutions are washed with N HCl and N NaOH, and dried (MgSO$_4$). Concentration of the ethyl acetate in vacuo leaves a residue (154 mg). This is chromatographed over 10 g of silica gel eluting with 50% to 60% ethyl acetate in hexane followed by 50% ethyl acetate in toluene. Fractions of 4 mL are collected. 5,5'-[2,5-furandiylbis(carbonylimino)]bis-1H-indole-2-carboxylic acid diethyl ester (107 mg) is obtained on evaporation of fr 22–50.

NMR: δ 1.413(t, 6H); 4.38(g, 4H); 7.137(s, 2H); 7.51(d, 2H); 7.58(d, 2H); 8.021(s, 2H); 8.097(bs, 2H); 10.146(bs, 2H); 11.742(bs, 2H). TLC: R$_f$=0.38 in (60-40) ethyl acetate-hexane.

Part B-Preparation of 5,5'-[2,5-furandiylbis(carbonylimino)]-bis-1H-indole-2-carboxylic acid.

5,5'-[2,5-furandiylbis(carbonylimino)]bis-1H-indole-2-carboxylic acid diethyl ester (60 mg, 0.11 mM) is suspended in methanol (0.4 mL) and treated with N NaOH (0.25 mL). After 5 days the reaction is evaporated in vacuo and the residue dissovlved in water and the solution acidified to pH 2 with N HCl. This solution is freeze dried leaving 5,5'-[2,5-furandiylbis(carbonylimino)]bis-1H-indole-2-carboxylic acid (22 mg).

Part C-Reaction of 5,5'-[2,5-furandiylbis(carbonylimino)] bis- 1H-indole-2-carboxylic acid with (Boc)CPI phenol chloride.

(S)-1-(chloromethyl)-1,6-dihydro-5-hydroxy-8-methyl-benzo[1,2-b: 4,3-b']dipyrrole-3(2H)-carboxylic acid 1,1-dimethyl ester [(Boc)CPI phenol chloride] (33 mg, 0.098 mM) is dissolved in ethyl acetate (1 mL) and the resultant solution stirred under an Ar atmosphere and treated with a freshly prepared saturated HCl solution in ethyl acetate (3 mL). After 45 min the mixture is evaporated in vacuo and the resultant (S)-1-(chloromethyl)-5-hydroxy-8-methyl-1,2,3,6-tetrahydro-benzo[1,2-b:4,3-b']dipyrrole hydrochloride (CPI phenol chloride hydrochloride) twice treated with CH$_2$Cl$_2$ and re-evaporated. This is treated with dimethylacetamide (1 mL) containing 5,5'-[2,5 -furandiylbis(carbonylimino]bis-1H-indole-2-carboxylic acid (22 mg, 0.047 mg). The resultant solution is treated in 2 portions about 50 min apart with EDC (40 mg, 0.21 mM). After 50 min the reaction is diluted with water and mixture extracted with THF-ethyl acetate. The combined organic layers are dried over MgSO$_4$ and concentrated in vacuo leaving a solid (15 mg). This material is chromatographed over silica gel (5 g) eluted with 20% to 30 % DMF in toluene. Fractions of 3 mL are collected. [S-(R*,R*]-N,N'-bis[2-[[1-(chloromethyl)-1,6 -dihydro-5-hydroxy-8-methylbenzo[1,2-b:4,3-b']dipyrrol-3(2H)-yl]-carbonyl]-1H-indol-5-yl]-2,5-furandicarboxamide (5 mg) is obtained on evaporation of fr 16–28.

NMR: δ 2.363(s, 6H); 3.60(m, 2H); 3.90(m, 2H); 4.03(m, 2H); 4.56(m, 2H); 4.68(m, 2H); 6.616(s, 1H); 7.05(s, 2H); 7.16(m, 2H); 7.41(s, 2H); 7.53(s, 4H); 7.64(m, 1H); 8.16(s, 2H); 9.79(s, 2H); 10.29(bs, 2H); 10.73(bs, 2H); 11.73(bs, 2H). UV: λmax (MeOH)=350 nm (ε=41000); 283 nm (ε=50500). MS(FAB): m/z 911 (M+H), 909 (M+H), 412. 395, 335, 300, 253, 210. TLC: R$_f$=0.217 in (20-80) DMF-toluene.

EXAMPLE 7

Preparation of [S-(R*,R*)]-N,N'-bis[2[[1-(chloromethyl)-1,6-dihydro-5-hydroxy-8-methylbenzo [1,2-b4,3-b']dipyrrol-3(2H)-yl]carbonyl]-1H-indol-5-yl]-1H-pyrrole-2,5-dicarboxamide (Compound 7)

Part A-Coupling of pyrrole-2,5-dicarboxylic acid to 5-amino-indole- 2-carboxylic acid ethyl ester.

Pyrrole-2,5-dicarboxylic acid (50 mg, 0. 32 mM, Kuhn, R. and Dury, K., *Justus Liebigs. Ann., Chem,.* 571, 44 (1951)) and 5-amino-indole- 2-carboxylic acid ethyl ester (130 mg, 0.64 mM) are dissolved in dimethylacetamide (2 mL) and the solution treated with EDC (129 mg, 0.67 mM). After 22 hrs the mixture is treated with ice water (20 mL) and the precipitated solid filtered. This material is chromatographed over silica gel (10 g), eluted with 10% to 15% DMF in toluene. Fractions of 4 mL are collected. A residue containing the product (72 mg) is obtained on evaporation of fr. 22–42. This residue is triturated with ethyl acetate and dried leaving 5,5'-[1 H-pyrrole-2,5-diylbis(carbonylimino)-bis-1H-indole-2-carboxylic acid diethyl ester (42 mg).

NMR: δ 1.413(t, 6H); 4:38(q, 4H); 7.137(s, 2H); 7.51(d, 2H); 7.58(d, 2H); 8.021 (s, 2H); 8.097(bs, 2H); 10.146(bs, 2H); 11,742(bs, 2H). TLC: R$_f$=0.38 in (60-40) ethyl acetate-hexane.

Part B-Preparation of 5,5'-[1H-pyrrole-2,5-diylbis(carbonylimino)-bis- 1H-indole-2-carboxylic acid 5,5'-[1H-pyrrole-2,5-diylbis(carbonylimino)-bis-1H-indole-2-carboxylic acid diethyl ester (42 mg, 08 mM) is dissolved in pyridine (1 mL) and the solution treated with N NaOH (0.2 mL). After 24 hrs the reation is treated with additional N NaOH (0.4 mL). After an additional 96 hrs the reaction is evaporated in vacuo and the residue dissolved in water (5 mL). The aqueous solution is acidified with N HCl to pH 2 and then freeze-dried, leaving 5,5'-[1H-pyrrole-2,5-diylbis(carbonylimino)-bis-1H-indole-2-carboxylic acid.

TLC: R$_f$=0.18 in (2-15-85) acetic acid-DMF-toluene.

Part C-Coupling of 5,5'-[1H-pyrrole-2,5-diylbis(carbonylimino)-bis- 1H-indole-2-carboxylic acid with (S)-1-(chloromethyl)-1,6 -dihydro-5-hydroxy-8-methyl-benzo[1,2-b:4,3-b']dipyrrole-3(2H)-carboxylic acid 1,1-dimethyl ester [(Boc)CPI phenol chloride]

(S)-1-(chloromethyl)-1,6-dihydro-5-hydroxy-8-methyl-benzo[1,2 -b:4,3-b']dipyrrole-3(2H) -carboxylic acid 1,1-dimethyl ester [(Boc)CPI phenol chloride] (40 mg, 0.12 nM) is dissolved in ethyl acetate (1 mL) under a nitrogen atmosphere. The reaction is treated with ethyl acetate freshly saturated with HCl (3 mL) and the resultant solution stirred at room temperature for 45 min. The solvent is removed in vacuo, and the residue returned to atmospheric pressure with nitrogen. The residue is twice re-evaporated with CH$_2$Cl$_2$ leaving (S)-1 -(chloromethyl)-5-hydroxy-8-methyl-1,2,3,6-tetrahydro-benzo[1,2-b:4,3-b']dipyrrole hydrochloride (CPI phenol chloride hydrochloride). This material is dissolved in dimethylacetamide (1 mL) and the solution treated with 5,5'-[1H-pyrrole-2,5-diylbis(carbonylimino)-bis-1H-indole-2-carboxylic acid (28 mg) and with EDC (25 mg, 0.13 mM). After 50 min the reaction is treated with additional EDC (25 mg). After another 50 min the reaction is diluted with water and the precipitated solids partitioned into THF-ethyl acetate. The combined organic layers are dried (MgSO$_4$) and concentrated in vacuo leaving a solid (80 mg). This material is chromatographed over of silica gel (10 g) eluted with 20% DMF in toluene. Fractions of 3 mL are collected. [S-(R*, R*)]-N,N'-bis[2[[1-(chloromethyl)-1,6-dihydro-5 -hydroxy-8-methylbenzo [1,2-b 4,3-b']dipyrrol-3(2H)-yl]carbonyl]-1H-indol- 5-yl]-1H-pyrrole-2,5-dicarboxamide (11 mg) is obtained on evaporation of fr 26–45.

NMR: δ 2.363(s, 6H); 3.60(m, 2H); 3.91(m, 2H); 4.032(m, 2H); 4.54(m, 2H); 4.68(m, 2H); 6.625(s, 1H); 7.05(s, 2H); 7.09(s, 2H); 7.13(s, 2H); 7.49(m, 4H); 7.64(m, 1H); 8.18(s, 2H); 9.78(s, 2H); 10.09 (bs, 2H); 10.72(bs, 2H); 11.67(bs, 2H); 12.22(bs, 1H). UV: $\lambda$max(methanol)=344 nm ($\epsilon$=58600); 296 nm ($\epsilon$=68000). MS(FAB): Calc'd for $C_{48}H_{39}Cl_2N_9O_6$; 908.2478; Found: 908.2496. ions at m/z 543, 368, 201. TLC: $R_f$=0.21 in (20-80)DMF-toluene.

EXAMPLE 8

Preparation of [R-(R*,S*)]-N,N'-bis[2-[[1-(chloromethyl)-1,6-dihydro-5-hydroxy-8-methylbenzo[1,2-b 4,3 -b']dipyrrol-3(2H)-yl]carbonyl]-1H-indol-5-yl]-propane-diamide (Compound 8)

Part A-Reaction of 5-aminoindole-2-carboxylic acid ethyl ester with malonyl dichloride.

A solution of 5-aminoindole-2-carboxylic acid ethyl ester (196 mg, 0.96 mM) in dry distilled THF (15 ml) is cooled in an ice bath under nitrogen. N,N-Diisopropylethylamine (350 μL, 2.01 mM) and malonyl dichloride (80 μL, 0.82 mM) are added by syringe. After one hour the solvent is partially removed and 5,5'-[(1,3-dioxo-1,3-propanediyl)-diimino]bis-1H-indole-2-carboxylic acid diethyl ester precipitated with water. The mixture is centrifuged, and the liquid layer withdrawn. The solid is dried under vacuum. The residue is chromatographed over silica gel (2 g) eluted with 25% acetone in toluene, 40% acetone in toluene, 60% acetone in toluene, 80% acetone in toluene and acetone. Fractions of 15 mL are collected. The product 5,5'-[(1,3-dioxo-1,3-propanediyl)-diimino]bis-1H-indole-2-carboxylic acid diethyl ester is found in fr 9–13 (77 mg).

NMR: (Acetone-d6) δ 1.37(t, 6H); 3.571(s, 2H); 4.36(q, 4H); 7.16(s, 2H); 7.48(m, 4H); 8.17(s, 2H); 9.71(bs, 2H); 10.92(bs, 2H). IR: 3300, 1650, 1200 cm$^{-1}$. UV: $\lambda$max=340 nm ($\epsilon$=5400); 297 nm ($\epsilon$=28000). MS(E1): m/z476(M+), 340, 272, 226, 204, 158. TLC: $R_f$=0.21 in (40-60) Acetone-hexane.

Part B-Preparation of 5,5'-[(1,3-dioxo-1,3-propanediyl)diimino]bis-1H-indole-2-carboxylic acid.

The diester of Part A (0.16 mM) is dissolved in pyridine (3 ml) and 1N sodium Hydroxide (0.53 ml). The reaction mixture is stirred under nitrogen at 50° C. for about 2 hours, then at room temperature for 4 hours. The reaction mixture is treated with 1N HCl and evaporated to near dryness. The product is precipitated with water and isolated by centrifugation, and washed with water, leaving 5,5'-[(1,3-dioxo-1,3-propanediyl)-diimino]bis-1H-indole-2-carboxylic acid.

NMR: δ 3.47(s,2H); 7.04(s,2H); 7.36(m,4H); 8.03(s,2H); 10.09(bs,2H); 11.68(bs,2H). UV: $\lambda$max=294 nm ($\epsilon$=13000).

Part C-Coupling of 5,5'-[(1,3-dioxo-1,3-propanediyl)diimino]-bis-1H-indole-2-carboxylic acid and (S)-1-(chloromethyl)-1,6-dihydro- 5-hydroxy-8-methyl-benzo[1,2-b:4,3-b']dipyrrole-3(2H)-carboxylic acid 1,1-dimethyl ester [(Boc)CPI phenol chloride].

(S)-1-(chloromethyl)-1,6-dihydro-5-hydroxy-8-methyl-benzo[1,2-b: 4,3-b']dipyrrole-3(2H)-carboxylic acid 1,1-dimethyl ester [(Boc)CPI phenol chloride] (37.8 mg, 0.11 mM) is dissolved in ethyl acetate (0.5 mL) under a nitrogen atmosphere. The solution is treated with HCl-saturated ethyl acetate (3 mL) for one hr. The reaction is evaporated, releasing the vacuum with nitrogen. The resultant (S)-1-(chloromethyl)-5-hydroxy-8-methyl-1,2,3,6-tetrahydro-benzo[1,2-b:4,3 -b']dipyrrole hydrochloride (CPI phenol chloride hydrochloride) is re-evaporated 2× with $CH_2Cl_2$. This material is treated with 5,5'-[(1,3-dioxo-1,3-propanediyl)diimino]bis-1H-indole-2-carboxylic acid, (24.3 mg, 0.058 mM) in dry dimethylacetamide (1 mL). EDC (49 mg, 0.156 mM) is weighed out and about one half is added to the reaction. The mixture is stirred at room temperature 45 min. Then the rest of the EDC is added, and stirring is continued 40 min. The reaction is diluted with ethyl acetate and water. The insoluble materials are removed by filtration and saved. The filtrate is separated into layers and the aqueous re-extrated with ethyl acetate. The combined organic layers are dried ($Na_2SO_4$) and concentrated in vacuum. The residue is combined with the filtered solids from above and are absorbed onto silica gel (0.4 g) and added to the top of a silica gel column (5 g). The column is eluted with 22% to 28% DMF in toluene, collecting fractions of 2 mL. The product 5,5'-[(1,3-dioxo-1,3-propanediyl)diimino]bis-1H-indole-2-carboxylic acid is isolated in fractions 14–28 (36 mg).

NMR: δ 2.354(s, 6H); 3.51(m, 2H); 3.60(m, 2H); 3.91(m, 2H); 4.03(m, 2H); 4.52(m, 2H); 4.67(m, 2H); 7.05(s, 2H); 7.10(s, 2H); 7.38(d, 2H); 7.46(d, 2H); 7.64(m, 2H); 8.10(s, 2H); 9.78(s, 2H); 10.13(bs, 2H); 10.72(bs, 2H); 11.64(bs, 2H). UV: $\lambda$max=336 nm($\epsilon$=35000); 294 nm ($\epsilon$=44000). TLC: $R_f$=0.46 in (30-70) DMF-toluene.

EXAMPLE 9

Preparation of [S-(R*,R*)]-6,6'-[carbonylbis(5-imino-1H-indole-2-carbonyl)]bis[8-(chloromethyl)-3,6,7,8-tetrahydro-1-methyl-benzo[1,2-b:4,3-b']dipyrrol-4-ol diacetate (Compound 9).

[7bR-[2(7'bR*,8'aS*),7bR*,8aS,]]-2,2'-[carbonylbis(imino-1 H-indole-5,2-dicarbonyl)]bis[1,2,8,8a-tetrahydro-7-methyl-cyclopropa(c)pyrrolo[3,2-e]indol-4(5H)-one (5 mg, 0.007 mM) is dissolved in DMF (200 μl) and acetone (0.5 ml) and the solution treated with pyridine hydrochloride (8.3 mg, 0.07 mM). The reaction is stirred at room temperature in the dark for 110 minutes and then concentrated to a small volume, and treated with water. The mixture is centrifuged and the liquids removed leaving [S-(R*,R*)]-6,6'-[carbonylbis(imino- 1H-indole-5,2-dicarbonyl)]bis[8-chloromethyl)-3,6,7,8-tetrahydro-1 -methyl-benzo[1,2-b:4,3-b'] dipyrrol-4-ol as a solid. The solid is dissolved in pyridine (100 μL) and treated with acetic anhydride (6 μL, 0.06 mM). The reaction is stirred in the dark at room temperature for 85 minutes, quenched with water and concentrated to dryness. The residue is treated with water and centrifuged. The liquid is removed and the solid dried under vacuum. This solid is adsorbed from DMF onto silica gel (0.07 g). Silica with absorbed compound is placed on a silica gel column (1 g), eluting with 10% to 40% DMF in toluene. Fractions of ½ mL are taken. [S-(R*,R*)]-6,6'-[carbonyl-bis( 5-imino-1H-indole-2-carbonyl)]bis[8-(chloromethyl)-3,6,7,8 -tetrahydro-1-methyl-benzo[1,2-b 4,3-b']dipyrrol-4-ol diacetate elutes in fractions 38–47 (3.4 mg).

NMR(DMSO-d6, TMS):δ 2.37 (s, 6H); 2.40(s, 6H); 3.72(m, 2H); 3.99 (m, 2H); 4.19 (m, 2H); 4.61(m, 2H); 4.74(m, 2H); 7.09 (s, 2H); 7.24 (m, 4H); 7.43 (m, 2H); 7.83 (bs, 2H); 7.87 (m, 2H); 8.50 (bs, 2H); 11.12 (bs, 2H); 11.56 (bs, 2H). UV(DMA+MeOH): λmax=325 nm ($\epsilon$=43,800); 294 nm ($\epsilon$=43,800).

EXAMPLE 10

Preparation of [S-(R*,R*)]-6,6'-(1H-indole-2,5-diyl-dicarbonyl)bis[8-(chloromethyl)-3,6,7,8-tetrahydro-1-methyl-benzo[1,2-b:4,3-b']dipyrrol-4-ol (Compound 10)

(S)-1-(chloromethyl)-1,6-dihydro-5-hydroxy-8-methyl-benzo[1,2-b: 4,3-b']dipyrrole-3(2H)-carboxylic acid 1,1-dimethyl ester [(Boc)CPI phenol chloride] (49 mg, 0.146 mM) is stirred at room temperature under nitrogen in ethyl acetate (0.6 mL). Ethyl acetate saturated with gaseous HCl (3 mL) is added and the reaction followed by TLC and is complete in about 45 minutes. The reaction is evaporated, releasing the vacuum with nitrogen. The resultant (S)-1-(chloromethyl)-5 -hydroxy-8-methyl-1,2,3,6-tetrahydro-benzo[1,2-b:4,3-b']dipyrrole hydrochloride (CPI phenol chloride hydrochloride) is re-evaporated 2× with $CH_2Cl_2$. The residual CPI phenol chloride hydrochloride salt is dissolved in dry dimethylacetamide (1 mL) and stirred at room temperature under nitrogen. Indole-2,5-dicarboxylic acid (15 mg, 0.073 mM) is added, followed by EDC (40 mg, 0.21 mM). After 45 minutes, additional EDC (23 mg, 0.12 mM) is added to the reaction mixture and which is then left to react for 1 hour. The reaction mixture is transferred to a centrifuge tube, rinsing in reaction with DMF (0.5 mL) and diluted with water to precipitate the product which is centrifuged and decanted. The crude product is transferred to a round bottom flask with acetone and the resulting solution evaporated under vacuum. The crude product is coated on silica gel (0.5 g) and chromatographed over a silica gel column (6 g) made up in 20% DMF in toluene and eluted with the same solvent collecting 1 ml fractions. [S-(R*,R*)]-6,6'-(1H-indole-2,5-diyldicarbonyl)bis[8-(chloromethyl)-3,6,7,8-tetrahydro-1-methyl-benzo[1,2-b:4,3-b']dipyrrol-4-ol is collected in fractions 22–47 and obtained on evaporation to dryness (31 mg).

NMR($d_6$-DMSO,TMS): δ 2.33(s, 3H); 2.36(s, 3H); 3.54–3.68(t, 2H); 3.79–3.96(m, 3H); 3.98–4.11(t, 2H); 4.23–4.44(bs, 1H); 4.50–4.60(d, 1H); 4.62–4.75(t, 1H); 7.02(s, 1H); 7.05(s, 1H); 7.22(s, 1H); 7.44–7.53(d, 1H); 7.53–7.62(d, 1H); 7.62–7.73(bs, 1H); 7.95(s, 1H); 7.98(s, 1H); 9.60–9.75(bs, 1H); 9.80(s, 1H); 10.66(s, 1H); 10.73(s, 1H); 11.93(s, 1H).

EXAMPLE 11

Preparation of [S-(R*,R*)]-N,N'-bis[2-[[1-(chloromethyl)-1,6-dihydro-5-hydroxy-8-methylbenzo[1,2-b:4,3-b']dipyrrol-3(2H)-yl]carbonyl]-1H-indol-5-yl]-1H-indole-2,5-dicarboxamide (Compound 11).

Part A-Preparation of 5,5'-[1H-indole-2,5-diylbis(carbonyl-imino)bis- 1H-indole-2-carboxylic acid diethyl ester.

Indole-2,5-dicarboxylic acid (200 mg, 0.49 mM) is stirred at room temperature under nitrogen in dry DMF (4 mL). To this is added 5-amino-indole-2-carboxylic acid ethyl ester (400 mg, 1.96 mM) and EDC (200 mg, 1.05 mM). After 3 days, the reaction mixture is transferred to a centrifuge tube and diluted with water. The precipitated solid is centrifuged and the supernatant liquid decanted. The residue is washed with acetone leaving 5,5'-[1H-indole-2,5 -diyl-bis(carbonylimino)bis-1H-indole-2-carboxylic acid diethyl ester (78 mg). Additional 5,5'-[1H-indole-2,5-diylbis(carbonylimino)bis-1 H-indole-2-carboxylic acid diethyl ester is obtained from the above acetone washings by concentration to dryness and chromatography over silica gel (40 g) eluting with 10%–20% DMF in toluene. Factions of 15 mL are collected and the 5,5'-[1H-indole-2,5-diylbis(carbonylimino)bis-1H-indole-2-carboxylic acid diethyl ester (83 mg) is obtained on evaporation to dryness of fractions 35–40.

Part B-Preparation of 5,5'-[1H-indole-2,5-diylbis(carbonylimino)]bis-1H-indole-2-carboxylic acid.

5,5'-[1H-indole-2,5-diylbis(carbonylimino)]bis-1H-indole-2-carboxylic acid diethyl ester (161 mg, 0.28 mM) is dissolved with stirring under nitrogen at room temperature in pyridine (5 mL) absolute ethanol (5 mL). To the resultant solution is added N NaOH (1 mL) and which is allowed to stand for 5 hr. The solvent is then mostly evaporated under vacuum, water is added, and the reaction mixture freeze-dried. The resultant crude product is coated on Celite (1.5 g) and added to the top of a C-18 reverse phase silica gel column (15 g). The column is eluted with the following: 50% DMF in water (200 mL); 60% DMF in water (100 mL); 70% DMF-30% water (100 ml); 80% DMF-20% water (300 ml). Fractions of 5 ml are collected, analyzing them by TLC. 5,5'-[1H-indole-2,5-diylbis(carbonylimino) ]bis-1H-indole-2-carboxylic acid (46 mg) is found in fractions 7–21.

Part C-Reaction of 5,5'-[1H-indole-2,5-diylbis(carbonylimino)]bis-1H-indole-2-carboxylic acid with (Boc)CPI phenol chloride.

(S)-1-(chloromethyl)-1,6-dihydro-5-hydroxy-8-methyl-benzo[1,2 -b: 4,3-b']dipyrrole-3(2H)-carboxylic acid 1,1-dimethyl ester [(Boc)CPI phenol chloride] (59 mg, 0.176 mM) is stirred at room temperature under nitrogen in dark for 45 min in ethyl acetate (1 mL) and ethyl acetate saturated with gaseous HCl (4 mL). TLC after 30 min shows reaction to be complete. The reaction mixture is evaporated under vacuum, and re-evaporated with $CH_2Cl_2$ 2×, letting in nitrogen each time giving (S)-1-(chloromethyl)-5-hydroxy-8-methyl-1,2,3,6-tetrahydro-benzo[1,2-b:4,3-b']dipyrrole hydrochloride (CPI phenol chloride hydrochloride). The CPI phenol chloride hydrochloride salt is dissolved with stirring under nitrogen in dark in dry DMA (1 mL). The solution is treated with 5,5'-[1H-indole-2,5-diylbis(carbonylimino)] bis-1H-indole-2-carboxylic acid (46 mg, 0.088 mM) and EDC (50 mg, 0.26 mM). After 30 min additional EDC is added (26 mg, 0.13 mM). The reaction is allowed to stand an additional 1 hr then transferred to a centrifuge tube and washed in with DMF (1 mL). Water is added to precipitate product which is then collected by centrifugation. The solid is washed into a RB flask with acetone and evaporated under vacuum. The residue is coated on silica gel (1 g) and chromatographed over a silica gel column (9 g). The column is eluted with 25% DMF in toluene followed by 30% and 40% DMF in toluene. Fractions of 2 ml are collected, and analyzed by TLC. [S-(R*,R*)]-N,N'-bis[2-[[1-(chloromethyl)-1,6-dihydro-5-hydroxy-8-methylbenzo-[1,2-b 4,3-b'] dipyrrol-3(2H)-yl]carbonyl]-1H-indol-5-yl]-1H-indole-2,5-dicarboxamide is found in fractions 31–80. Impure product is found in fractions 8–30. These are rechromatographed over a silica gel column (4.5 g) eluted with 20% DMf in toluene to 30% DMF in toluene. Fractions of 1 mL are collected. [S-(R*,R*)]-N,N'-bis[2-[[1-(chloro-methyl)- 1,6-dihydro-5-hydroxy-8-methylbenzo[1,2-b 4,3-b']dipyrrol-3(2H)-yl]carbonyl]-1H-indol-5-yl]-1H-indole-2,5-dicarboxamide is found in fractions 25–75. Combination of the material from the two chromatographies gives [S-(R*,R*)]-N,N'-bis[2-[[1-(chloromethyl)-1,6 -dihydro-5-hydroxy-8-methylbenzo[1,2-b 4,3-b']dipyrrol-3(2H)-yl]carbonyl]-1H-indol-5-yl]-1H-indole-2,5-dicarboxamide (47 mg).

NMR($d_6$-DMSO,TMS): δ 2.37(s, 6H); 3.55–3.68(t, 2H); 3.87– 3.97(d, 2H); 3.97–4.10(t, 2H); 4.51–4.61(d, 2H);

4.61–4.77(t, 2H); 7.07(s, 2H); 7.14(s, 1H); 7.17(s, 1H); 7.45–7.75(m, 8H); 7.96(s, 1H); 8.23(s, 2H); 8.26(s, 1H); 8.46(s, 1H); 9.82(s, 2H); 10.18(s, 1H); 10.33(s, 1H); 10.75(s, 2H); 11.66(s, 1H); 11.71(s, 1H); 12.09(s, 1H).

UV(DMA+MeOH): λmax=328 nm (ε=33,560); 281 nm (ε=38,350)

EXAMPLE 12

Preparation of [S-(R*,R*)]-2-[[1-(chloromethyl)-1,6-dihydro-5-hydroxy-8-methyl-benzo[1,2-b:4,3-b']dipyrrol-3(2H)-yl]-carbonyl]-N-[2-[[1-(chloromethyl)-1,6-dihydro-5-hydroxy-8-methylbenzo[1,2-b:4,3-b']dipyrrol-3(2H)-yl]carbonyl]-1H-indol-5-yl]-1H-indole-5-carboxamide (Compound 12)

Part A-Preparation of 5-[[(2-carboxy-1H-indol-5-yl)amino]carbonyl]-1H-indole-2-carboxylic acid Indole-2,5-dicarboxylic acid (98 mg, 0.42 mmoles) and 5-amino-indole- 2-carboxylic acid ethyl ester (86 mg, 0.42 mM) are stirred at room temperature under nitrogen in dry DMF (2 mL). EDC (90 mg, 0.47 mM) is added and left to react for 25 hr. The reaction mixture is diluted with water and centrifuged and the supernatant is decanted. The residual solid is dissolved in acetone and re-evaporated and then is chromatographed over silica gel (20 g), and eluted with 50% ethyl acetate in hexane followed by 30% acetone in hexane. Fractions of 15 ml are collected, and analyzed by TLC. 5-[[(2-carboxy-1H-indol-5-yl)amino]carbonyl]-1H-indole-2-carboxylic acid diethyl ester is found in fractions 8–86 (137 mg, 78% yield).

Part B-Preparation of 5-[[(2-carboxy-1H-indol-5-yl)amino]carbonyl]-1H-indole-2-carboxylic acid 5-[[(2-carboxy-1H-indol-5-yl)amino]carbonyl]-1H-indole-2-carboxylic acid diethyl ester (137 mg, 0.33 mM) is dissolved with stirring at room temperature under nitrogen in pyridine (3 mL) and absolute ethanol (3 mL). 1N NaOH (1 mL) is added and the reaction left to react for 29 hr during which time a precipitate forms. 1N HCl (1 mL) is added and the reaction mixture concentrated on a rotary evaporator. Water is added to the residue, forming a cloudy solution. The solution is freeze-dried. The residue is coated on celite (1 g) which is then added to the top of a C-18 reversed phase silica gel column (10 g). The column is eluted with 40% DMF water to 80% DMF water in 10% increments (100 mL each). Fractions of 5 mL are collected. 5-[[(2-carboxy-1H-indol-5-yl)amino]carbonyl]-1 H-indole-2-carboxylic acid is found in fractions 30–70 (40 mg).

Part C-Reaction of 5-[[(2-carboxy-1H-indol-5-yl)amino]carbonyl]-1H-indole-2-carboxylic acid with (Boc)CPI phenol chloride (S)-1-(chloromethyl)-1,6-dihydro-5-hydroxy-8-methyl-benzo[1,2 -b:4,3-b']dipyrrole-3(2H)-carboxylic acid 1,1-dimethyl ester [(Boc)CPI phenol chloride] (74 mg, 0.22 mM) is stirred at room temperature under nitrogen in dark for 45 min in ethyl acetate (1 mL) and the ethyl acetate saturated with gaseous HCl (5 mL). The reaction mixture is evaporated under vacuum, and re-evaporated with CH₂Cl₂ 2×, letting in nitrogen each time leaving (S)-1-(chloromethyl)-5-hydroxy- 8-methyl-1,2,3,6-tetrahydro-benzo[1,2-b:4,3-b']dipyrrole hydrochloride (CPI phenol chloride hydrochloride). The CPI phenol chloride hydrochloride salt is dissolved with stirring under nitrogen in dark in dry DMA (1 mL). 5-[[(2-carboxy-1H-indol-5-yl)amino]carbonyl]-1 H-indole-2-carboxylic acid (40 mg, 0.11 mM) and EDC (75 mg, 0.39 mM) are added to the reaction and left to react for 30 min, when additional EDC (20 mg, 0.10 mM) is added and left to react for 1 hr more. The solution is transferred to a centrifugal tube and washed in with DMF (1 mL), diluted with water to precipitate product, and centrifuged. The supernatant is decanted. The solid is washed into RB flask with acetone and re-evaporated under vacuum.

The crude product is coated on silica gel (1 g) and placed on top of a silica gel column (9 g) made up in 20% DMF-80% toluene. The column is eluted with 20% DMF in toluene, followed by 30% DMF in toluene. Fractions of 2 ml are collected. Fractions 21–78 are collected and evaporated and the residue rechromatographed over a silica gel column (5 g) eluted with 20% DMF in toluene. Fractions of 1 mL are collected. [S-(R*,R*)]-2-[[1-(chloromethyl)-1,6-dihydro-5-hydroxy-8'methyl-benzo[1,2-b:4,3-b']dipyrrol-3(2H)-yl]-carbonyl]-N-[2-[[1-(chloromethyl)-1,6-dihydro-5-hydroxy-8-methylbenzo[1,2-b:4,3 -b']dipyrrol-3(2H)-yl]carbonyl]-1H-indol-5-yl]-1H-indole-5-carboxamide is found in fractions 20–45 (49 mg, 56% yield).

NMR(d₆-DMSO,TMS): δ 2.37(s, 6H); 3.54–3.68(t, 2H); 3.87– 3.97(d, 2H); 3.98–4.10((t, 2H); 4.50–4.60(d, 2H); 4.61–4.77(q, 2H); 7.07(s, 2H); 7.13(s, 1H); 7.29(s, 1H); 7.45–7.52(d, 1H); 7.55–7.73(m, 4H); 7.91(s, 1H); 8.23(s, 1H); 8.45(s, 1H); 9.82(s, 1H); 9.84(s, 1H); 10.18(s, 1H); 10.75(s, 1H); 10.76(s, 1H); 11.65(s, 1H); 12.00(s, 1H).
UV(DMA+MeOH): λmax=328 nm (ε=36,830); 292nm sh (ε=43,800)

EXAMPLE 13

Preparation of [S-(R*,R*)]-5-[[1-(chloromethyl)-1,6-dihydro-5-hydroxy-8-methylbenzo[1,2-b:4,3-b']dipyrrol-3(2H)-yl]-carbonyl)-N-[2-[[1-(chloromethyl)-1,6-dihydro-5-hydroxy-8-methylbenzo[1,2-b:4,3-b']dipyrrol-3(2H)-yl]carbonyl)-1H-indol-5-yl]-1H-indole-2-carboxamide (Compound 13).

Part A-Preparation of 5-[[[(5-carboxy-1H-indol-2-yl)carbonyl]amino]-1H-indole-2-carboxylic acid diethyl ester Indole-2,5-dicarboxylic acid 5-ethyl ester (65 mg, 0.28 mM) is stirred at room temperature under nitrogen in dry DMF(1 mL). 5-Amino-indole- 2-carboxylic acid (57 mg, 0.28 mM) and EDC (60 mg, 31 mM) are added. After 24 hr the reaction is diluted with water and the solids collected by filtration. The residual solid is dissolved in acetone and evaporated onto silica gel (2 g). This material is added to the top of a silica gel column (18 g) and eluted with 10% DMF in toluene. 5-[[(5-carboxy-1H-indol-2-yl)carbonyl]amino]-1H-indole- 2-carboxylic acid diethyl ester (75 mg, 64% yield) is found in fractions.

Part B-Preparation of 5-[[(5-carboxy-1H-indol-2-yl)carbonyl]amino]-1H-indole-2-carboxylic acid 5-[[(5-carboxy-1H-indol-2-yl)carbonyl]amino]-12H-indole-2 -carboxylic acid diethyl ester (75 mg, 0.18 mM) is stirred at room temperature under nitrogen in pyridine (2 mL), absolute ethanol (2 mL) and 1N NaOH (600 μL) for 120 hr at 25° C. Additional 1N NaOH (1 mL) is then added and the reaction heated for 20 hr at 50° C. 1N HCl (1.6 mL) is then added and the reaction evaporated under vacuum. The residue is coated on Celite (1 g) and placed in an C-18 silica gel column (10 g). The column is eluted with 508 DMF in water to 80% DMF in water (100 ml each in 108 increments). Fractions of 5 ml are collected and analyzed by TLC. 5-[[(5-carboxy-1H-indol-2-yl)carbonyl]amino]-1H-indole-2-carboxylic acid is found in fractions 5–77.

Part C-Reaction of 5-[[(5-carboxy-1H-indol-2-yl)carbonyl]amino]-1H-indole-2-carboxylic acid with (Boc)CPI phenol chloride (S)-1-(chloromethyl)-1,6-dihydro-5-hydroxy-8-methyl-benzo[1,2 -b:4,3-b']dipyrrole-3(2H)-carboxylic acid 1,1-dimethyl ester [(Boc)CPI phenol chloride] (121 mg, 0.36 mM) is stirred at room temperature under nitrogen in dark for 30 min in ethyl acetate (2 mL) and ethyl acetate saturated with gaseous HCl (8 mL). TLC after 30 min shows the reaction to be complete. The reaction is evaporated under vacuum and re-evaporated with $CH_2Cl_2$×, letting in nitrogen each time giving (S)-1-(chloromethyl)-5-hydroxy-8-methyl-1,2,3,6-tetrahydro-benzo[1,2-b:4,3-b']dipyrrole hydrochloride (CPI phenol chloride hydrochloride). The CPI phenol chloride hydrochloride salt is dissolved with stirring under nitrogen in the dark in dry DMA (1.5 mL). 5-[[(5-carboxy-1H-indol-2-yl)carbonyl]amino]-1H-indole-2 -carboxylic acid (65 mg0 0.18 mM) and EDC (110 mg, 0.57 mM) are added to the resultant solution. After 30 min reation is treated with additional EDC (45 mg, 0.23 mM) and left to react 1.5 hr more. The reaction solution is transferred to a centrifuge tube and washed in with DMF (1 mL), diluted with water to precipitate product, and centrifuged. The supernatant is decanted. The solid is washed into RB flask with acetone and re-evaporated under vacuum. The crude product is coated on silica gel (1 g) and placed on top of a silica gel column (10 g) made up in 20% DMF-808 toluene. The column is eluted with 20% DMF in toluene, followed by 358 DMF in touene. Fractions of 2 ml are collected. [S-(R*, R*)]-5-[[1-(chloromethyl)- 1,6-dihydro-5-hydroxy-8-methylbenzo[1,2-b:4,3-b']dipyrrol-3(2H)-yl]-carbonyl)-N-[2-[[1-(chloromethyl)-1,6-dihydro-5-hydroxy-8-methyl-benzo[1,2-b:4,3-b']dipyrrol-3(2H)-yl]carbonyl)-1H-indol-5-yl]-1H-indole- 2-carboxamide (43 mg) is isolated from fractions 25–47.

NMR($d_6$-DMSO,TMS): δ 2.33(s, 3H); 2.37(s, 3H); 3.50–3.70(t, 2H); 3.78–3.97(m, 3H); 3.97–4.14(t, 2H); 4.24–4.43(bs, 1H); 4.48–4.62(d, 1H); 4.62–4.75(t, 1H); 7.04(s, 1H); 7.06(s, 1H); 7.16(s, 1H); 7.40– 7.72(m, 7H); 8.00(s, 1H); 8.25(s, 1H); 9.64–9.80(bs, 1H); 9.81(s, 1H); 10.30(s, 1H); 10.68(s, 1H); 10.75(s, 1H); 11.70(s, 1H); 12.03(s, 1H). UV(DMA+MeOH): λmax=316 nm sh (ε 36,830); 295 nm (ε=40,030)

EXAMPLE 14

Preparation of [S-(R*,R*)]-carbonylbis[imino-1H-indole-5,2-diylcarbonyl[1-(chloromethyl)-1,6-dihydro-8-methylbenzo[1,2-b:4,3-b']dipyrrole-3,5(2H)-diyl]]-ester, 2,2-dimethylpropanoic acid (Compound 14)

[7bR-[2(7'bR*,8'aS*),7bR*,8aS*]]-2,2'-[carbonylbis(imino-1 H-indole-5,2-dicarbonyl)]bis[1,2,8,8a-tetrahydro-7-methyl-cyclopropa(c)pyrrolo[3,2-e]indol-4(5H)-one (5.4 mg, 7.3 μM) is dissolve in pyridine (200 μL) and the the solution treated with 2,2-dimethylpropionic acid chloride (24 μL, 192 μM) at 0 C. After 10 minutes the reaction is warmed to 25 C and is stirred 20 min at that temperature. The reaction is then quenched with water (0.1 mL) and concentrated to dryness. The residue is dissolved in DMF and evaporated under vacuum onto silica gel (0.1 g). This material is added to the top of a silica gel column (1 g) and eluted with 10% to 30% DMF in toluene. Fractions of 0.2 mL are collected. Fractions 17–50 are evapoarated to dryness and the residue washed with acetone. The residue from the acetone wash is then chromatographed over a silica gel column (0.3 g) eluted with 10%–12% DMF in toluene. Fractions of 0.2 mL are collected. [S-(R*,R*)]-carbonylbis[imino-1H-indole-5,2-diylcarbonyl[1 -(chloromethyl)-1,6-dihydro-8-methylbenzo[1,2-b:4,3-b']dipyrrole- 3,5(2H)-diyl]]ester, 2,2-dimethylpropanoic acid (1.1 mg) is obtained on evaporation of fr 9–23.

NMR($d_6$-DMSO,TMS): δ 1.39(s, 18H); 2.41 (s, 6H); 3.73 (m, 2H); 4.00 (m, 2H); 4.21 (m, 2H); 4.60 (m, 2H); 4.73(m, 2H); 7.09 (s, 2H); 7.25 (m, 4H); 7.42 (m, 2H); 7.80 (bs, 2H); 7.88 (s, 2H); 8.55 (bs, 2H); 10.87 (bs, 2H); 11.54 (bs, 2H). UV(DMA+MeOH): λmax=324 nm (ε=40,000); 294 nm (ε=40,000).

EXAMPLE 15

Preparation of [S-(R*,R*)]-carbonylbis[imino-1H-indole-5,2-diylcarbonyl[1-(chloromethyl)-1,6-dihydro-8-methylbenzo[1,2-b:4,3-b']dipyrrole-3,5(2H)-diyl]]-ester, decanoic acid (Compound 15).

[S-(R*,R*)]-6,6'-[carbonylbis(imino-1H-indole-5,2-dicarbonyl)]-bis[8-chloromethyl)-3,6,7,8-tetrahydro-1-methyl-benzo[1,2-b:4,3-b']dipyrrol-4-ol (10 mg, 0.012 mM) is dissolved in pyridine (0.2 mL) and DMF (0.01 mL). The solution is treated with decanoic anydride (75 mg, 0.23 mM) and the reaction stirred in the dark for 24 hr. The reaction is then quenched with water (0.05 mL) and evaporated to dryness. The residue is washed with water and with toluene each the insolubles are collected by centrifugation. The resultant residue is chromatographed over a silica gel column (1.2 g) eluted with 5%, 6%, 7%, and 10% DMF in toluene. Fractions of 0.3 mL are collected. [-S(R*,R*)]-carbonylbis[imino-1H-indole-5,2-diylcarbonyl[1-(chloromethyl)- 1,6-dihydro-8-methylbenzo[1,2-b:4,3-b']dipyrrole-3,5(2H)-diyl]]ester, decanoic acid (1.3 mg) is obtained on evaporation of fractions 18–60.

NMR($d_6$-DMSO,TMS): δ 0.86 (t); 1.24 (m); 1.45 (m); 2.18 (t); 2.40(s); 3.70 (m); 3.98(m); 4.15 (m); 4.59 (m); 4.71 (m); 7.08 (s); 7.27 (m); 7.42 (m); 7.80 (m); 7.88 (s); 8.59 (bs); 11.05 (bs); 11.53 (bs). UV(DMA+MeOH): λmax=324 nm (ε=40,000); 294 nm (ε=40,000).

EXAMPLE 16

Preparation of [S-(R*,R*)]-6,6'-[carbonylbis[(7,8 -dihydrobenzo[1,2-b:4,3-b']dipyrrole-6,2(3H)-diyl)-carbonyl]]bis[8-(chloromethyl)-3,6,7,8-tetrahydro-1-methyl-benzo[1,2-b:4,3b']dipyrrol-4-ol (Compound 16)

Part A-Preparation of 6,6'-carbonylbis[3,6,7,8-tetrahydrobenzo[1,2-b:4,3-b']dipyrrole-2-carboxylic acid ethyl ester is described in M. A. Warpehoski, V. S. Bradford, Tetrahedron Lett, 1986, 27, 2735.

NMR: δ 1.35(t, 6H) 3.285(t, 4H); 4.123(t, 4H); 4.34(q, 4H); 7.06(s, 2H); 7.22(d, 2H); 7.32(d, 2H); 11.845(s, 2H). MS(EI): m/z 586(M+), 257, 230, 184, 156. TLC: $R_f$=0.14 in (25-75) Acetone-hexane.

Part B-Preparation of 6,6'-carbonylbis[3,6,7,8-tetrahydrobenzo[1,2-b:4,3-b']dipyrrole-2-carboxylic acid diethyl ester.

6,6'-carbonylbis[3,6,7,8-tetrahydro-benzo[1,2-b:4,3-b'] dipyrrole-2-carboxylic acid ethyl ester (30 mg, 0.13 mM) is dissolve in dry THF (0.5 mL) and the solution treated with 4-dimethylaminopyridine (1 mg). This solution is cooled to −98° C. in a liquid nitrogen-frozen methanol bath under nitrogen. Diisopropylethylamine is added (25 μl, 0.14 mM)

followed by 1.93M phosgene in toluene (35 μl, 0.067 mM). The reaction is stirred at about −98° C. for 3 hr. It is then stored in the −65° C. freezer overnight. The reaction is allowed to stir at room temperature for 90 min. It is diluted with water and ethyl acetate. The ethyl acetate layer is washed with brine, dried and evaporated. The crude residue (47.9 mg) is adsorbed onto silica gel (0.5 g) from distilled THF. The resultant solid is added to the top of a silica column (5 g) and eluted with 5%–15% acetone in toluene. Fractions are of 3 mL are collected. 6,6'-carbonylbis[3,6,7,8-tetrahydrobenzo[1,2-b:4,3-b']dipyrrole-2-carboxylic acid diethyl ester (5.6 mg) is found in fraction 5–9.

Part C-6,6'-carbonylbis[3,6,7,8-tetrahydrobenzo[1,2-b:4,3-b']dipyrrole-2-carboxylic acid diethyl ester (7 mg, 0.014 mM) is dissolved in pyridine and the solution treated with 1N NaOH (0.05 mL). The reaction is then heated to 50 C for 6 hr. The reaction is acidified with 1N HCl (0.2 mL) and 6,6'-carbonylbis[3,6,7,8-tetrahydrobenzo[1,2-b:4,3-b'] dipyrrole-2-carboxylic acid diethyl ester precipitated as a solid is collected by centrifugation and dried under vacuum.

Part D-Preparation of [S-(R*,R*)]-6,6'-[carbonylbis[(7,8-dihydrobenzo[1,2-b:4,3-b']dipyrrole-6,2(3H)-diyl)carbonyl]]bis[8 -(chloromethyl)-3,6,7,8-tetrahydro-1-methyl-benzo[1,2-b:4,3b']dipyrrol- 4-ol (Compound 16).

(S)-1-(chloromethyl)-1,6-dihydro-5-hydroxy-8-methyl-benzo[1,2b:4,3-b']dipyrrole-3(2H) -carboxylic acid 1,1-dimethyl ester [(Boc)CPI phenol chloride] (11 mg, 0.033 mM) is dissolved in ethyl acetate (0.2) and HCl-saturated ethyl acetate (0.7 mL). The mixture is stirred at room temperature under nitrogen for 1 hr. It is evaporated under a nitrogen stream. $CH_2C_{12}$ is added, and the residual (S)-1-(chloromethyl)-5-hydroxy-8-methyl-1,2,3,6-tetrahydrobenzo[1,2-b:4,3-b']dipyrrole hydrochloride (CPI phenol chloride hydrochloride salt) is re-evaporated twice under a nitrogen stream. 6,6'-carbonylbis[3,6,7,8-tetrahydrobenzo[1,2-b:4,3-b']dipyrrole-2-carboxylic acid diethyl ester (6 mg, 0.014 mM) is dissolved in DMA (0.3 mL) and added to the CPI phenol chloride hydrochloride salt. Then the mixture is treated with EDC (6.4 mg, 0.034 mM). The reaction is stirred under nitrogen at room temperature 50 min. Additional EDC (6.4 mg, 0.034 mM) is added, and stirring is continued 65 min. The product is precipitated out by the gradual addition of water. The solids (28 mg) are collected by centrifugation and dried under vacuum. This crude product is adsorbed from DMF onto silica gel (0.3 g). It is put on a silica gel column (3 g), eluting with 10, 12, 14, 16 and 20% DMF-toluene. Fractions of 1 mL are collected. [S -(R*,R*)] -6,6'-[carbonylbis[(7,8-dihydrobenzo[1,2-b:4,3-b']dipyrrole- 6,2(3H)-diyl)carbonyl]]bis [8-(chloromethyl)-3,6,7,8-tetrahydro- 1-methyl-benzo[1,2-b:4,3b']dipyrrol-4-ol (6 mg) is obtained on concentration of fractions 40–62.

NMR: δ 2.36(s, 6H); 3.3(t, 4H); 3.61(m, 2H); 3.92(m, 2H); 4.03(m, 2H); 4.16(t, 4H); 4.55(m, 2H); 4.69(m, 2H); 7.01(s, 2H); 7.05(s, 2H); 7.27(m, 4H); 7.66(m, 2H); 9.79(s, 2H); 10.74(bs, 2H); 11.62(bs, 2H). UV: λmax=353 nm (ε=28000); 286 nm(ε=45000). TLC: $R_f$=0.29 in (20-80) DMF-toluene.

The starting compounds are known or can be readily prepared by known methods. See M. A. Warpehoski, Tet. Lett., 27, 4103 (1986); W. W. Wierenga, J. Am. Chem. Soc., 103, No. 18, 1981; D. G. Martin, J. Antibiotics 1985, 38, 746; and M. A. Warpehoski, I. Gebhart, R. C. Kelly, W. C. Krueger, L. H. Li, J. P. McGovren, M. D. Prairie, N. Wicnienski and W. Wierenga, J. Med. Chem., 1988, 31, pp. 590–603.

The preparation of CPI(Boc) HCl is described in R. C. Kelly, I. Gebhard, N. Wicnienski, P. A. Aristoff, P. D. Johnson, D. G. Martin, J. Am. Chem. Soc. 1987, 109 6837.

The spirocyclopropylcyclohexadienyl compounds of Formula A and 1-(halomethyl)-1,6-hydro-5-hydroxy-8-methyl-benzo[1,2-b:4,3-b']dipyrrole- 3(2H)-yl 5-ester or urethanes (Formula B) can also be prepared by the procedures and methods disclosed in U.S. patent application Ser. No. 894,314, filed Aug. 7, 1986 (now abandoned), and PCT/87/03227 patent application filed Dec. 11, 1987. Both are incorporated herein by reference. See also EP Application 0 154 445 (published 9 Nov. 1985).

All the compounds of the subject invention have UV absorption in the range of 200 nm to 380 nm. Thus, novel compounds of the subject invention (Formula I) are useful as UV adsorbents in technical and industrial areas, as follows:

(a) textile materials, for example, wool, silk, cotton, hemp, flax, linen and the like;

(b) natural or synthetic resins.

Depending on the nature of the material to be treated, the requirements with regard to the degree of activity and durability, and other factors, the proportion of the light screening agent to be incorporated in the material may vary within fairly wide limits, for example, from about 0.01% to about 10%, and, advantageously, 0.1% to 2% of the weight of the material which is to be directly protected against the action of UV rays.

The compounds of Formula I are particularly useful as antitumor agents. Examples of compounds of Formula I demonstrate antitumor activity in P388 leukemic mice, and also show significant activity in the L1210 leukemia and B16 melanoma murine test systems. These murine test systems are predictive for clinically useful human antitumor agents (see, for example, A. Geldin et al, European J. Cancer, Vol. 17, pp 129–142, 1981; J. M Vendetti, Cancer Treatment Reports, Vol. 67, pp. 767–772, 1983; and J. M. Vendetti et al, Advances in Pharmacology and Chemotherapy, Vol. 20, pp. 1–20, 1984), and, therefore, the compounds of the subject invention (Formula I) will be useful in the control and treatment of susceptible neoplastic (cancer) diseases, including susceptible leukemics, in humans when given, for example, intravenously in doses of 0.001 μg/kg to about 10 mg/kg of body weight per day, the exact dose depending on the age, weight, and condition of the patient, and on the frequency of administration.

The compounds of Formula I are effective when administered intravenously (IV) in fluid solutions by bolus injection or by infusion. The preferred doses are 0.01 microgram/kg to 1000 microgram/kg by bolus injection and 0.0002 to 20 microgram/kg/min by infusion. The exact dose will vary depending on the particular compound as well as the age, weight, route of administration, and physical condition of the patient, and on the frequency of administration.

Illustrative in vivo and in vitro L1210 testing data on the compounds of Formula I are presented in Tables 1 and 2. Table 3 presents data comparing [S-(R*,R*)]-6,6'-[carbonylbis(imino-1 H-indole-5,2-dicarbonyl)]bis[8-chloromethyl)-3,6,7,8-tetrahydro-1 -methyl-benzo[1,2-b:4,3-b'] dipyrrol-4-ol (Compound 1) with (7bR)-N-[2-[(4,5,8,8a-tetrahydro-7-methyl-4-oxocyclopropa-[c]pyrrolo[3,2-e]-indol-2(1H)Oyl)carbonyl]-1H-indol-5-yl]-2-benzofurancarboxamide (U- 73,975) in the other murine systems where the compounds have been run jointly. Compound 1 is as least as active as the compound U-73,975 in every system and in some such as the subcutaneous L1210 assay it shows superior activity over several dose ranges. Further, Compound 1, like U-73,975, has been found not to cause delayed death.

In vivo L1210 biological data shows [S-(R*,R*)]-6,6'-[carbonyl-bis(imino- 1H-indole-5,2-dicarbonyl)]bis[8-chloromethyl)-3,6,7,8-tetrahydro-1-methyl-benzo[1,2-b:4,3-b']dipyrrol-4-ol (Compound 1) to be the most active analog being highly curative at 15 µg/kg. The results set forth in Tables 1 and 4 were obtained using standard well known procedures (In Vivo Cancer, Models, NIH Publication No. 84-2635, 1984).

T/C refers to median life span of treated mice divided by median life span of control mice times 100.

The compounds of formula I are useful as antibacterial agents. These compounds are useful to control the proliferation of susceptible microbes in various environments using standard microbiological techniques. Such environments include dental utensils contaminated with *S. aureus*, and the like, and laboratory benches in a microbiological laboratory which can be cleansed with a formulation containing about 1–10% (w/v) of a compound of formula I.

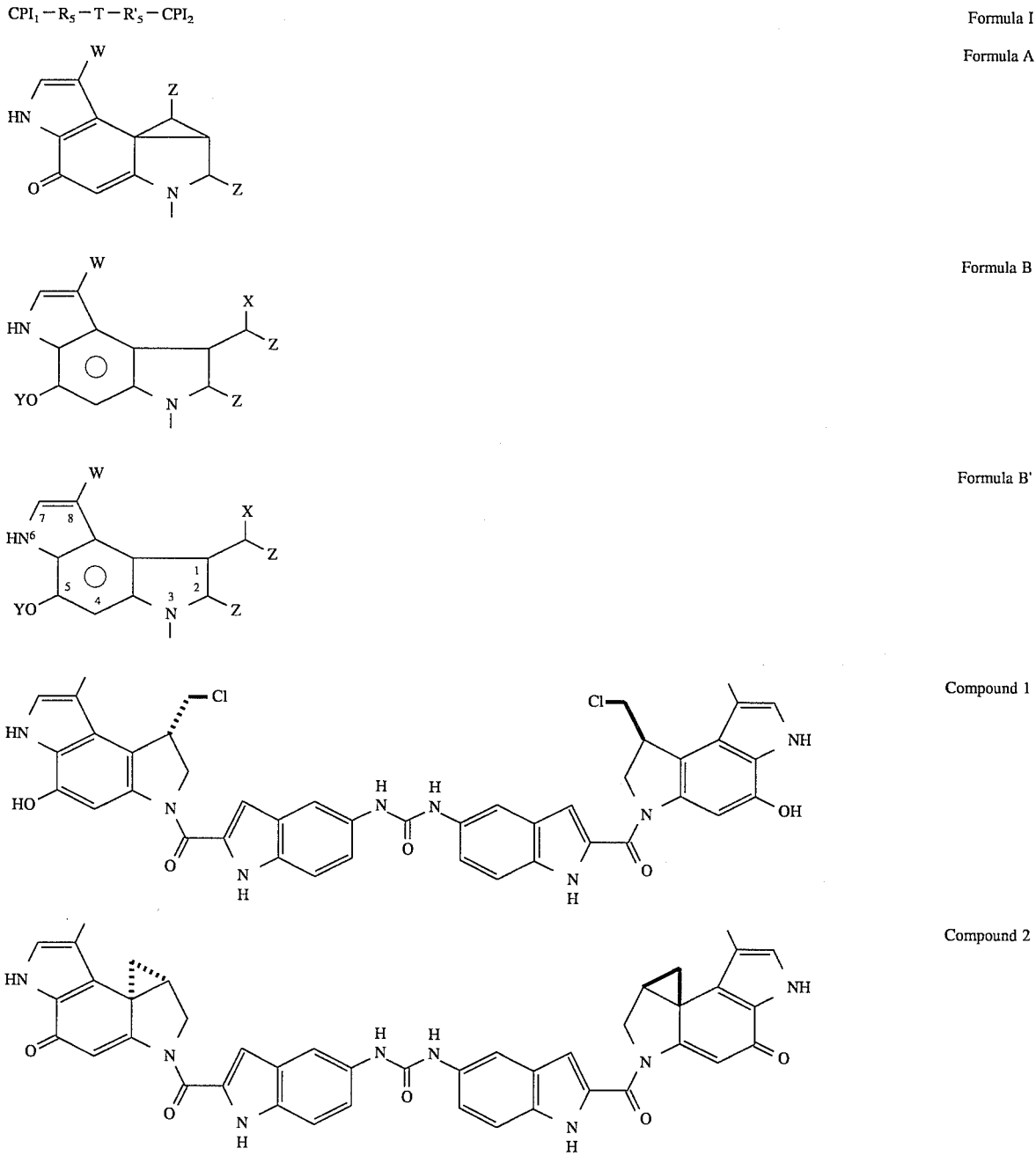

-continued
GENERAL FORMULA CHART
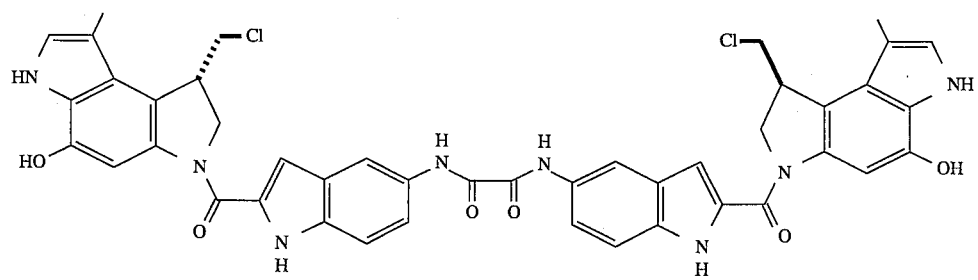
Compound 3
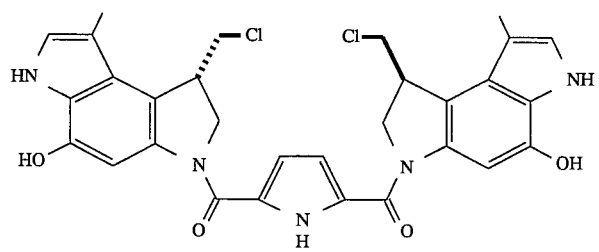
Compound 4
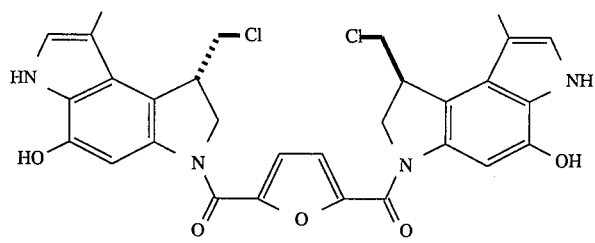
Compound 5
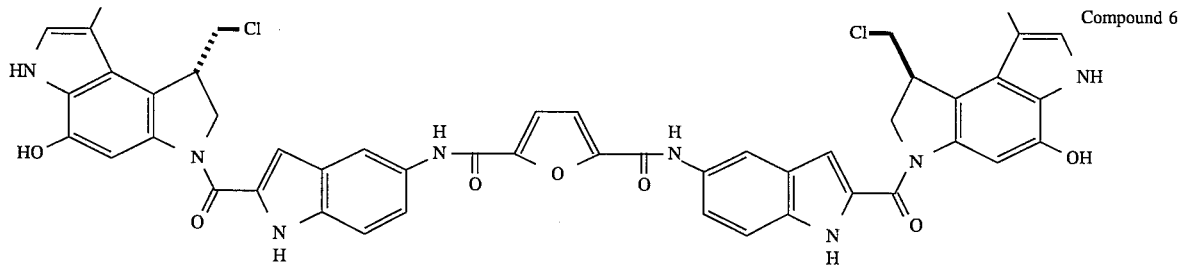
Compound 6
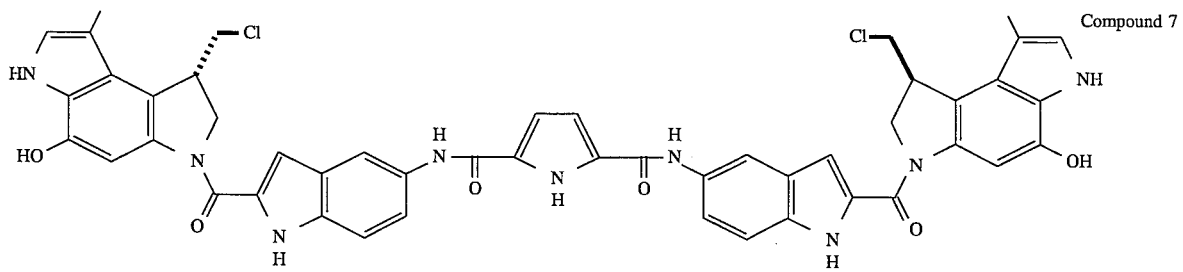
Compound 7
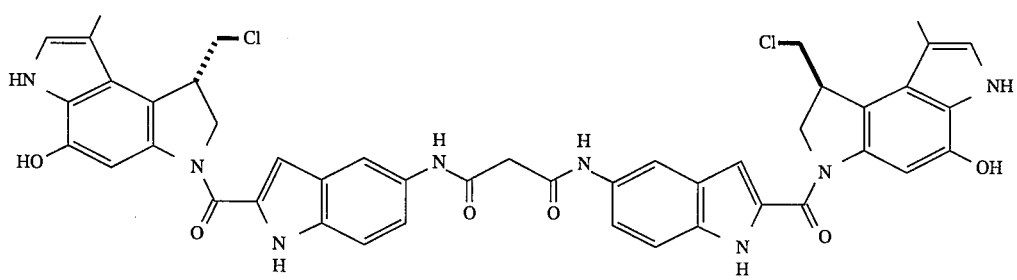
Compound 8

-continued
GENERAL FORMULA CHART
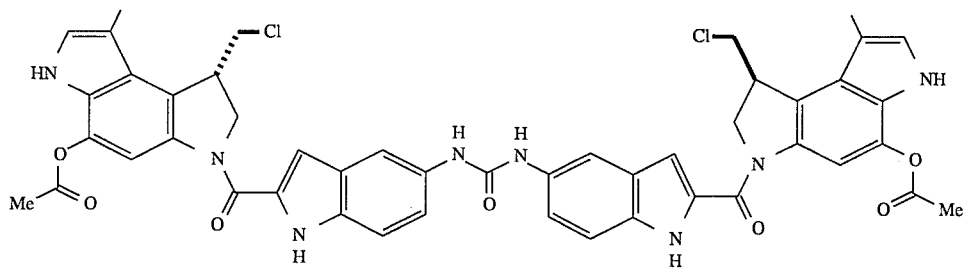
Compound 9
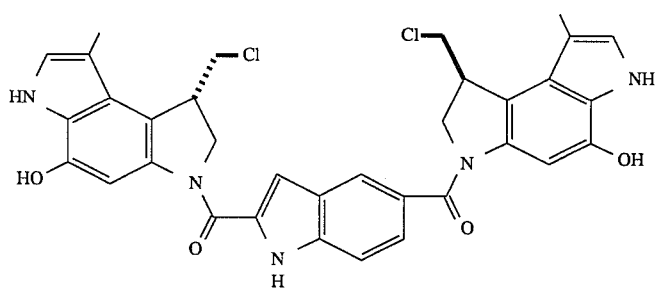
Compound 10
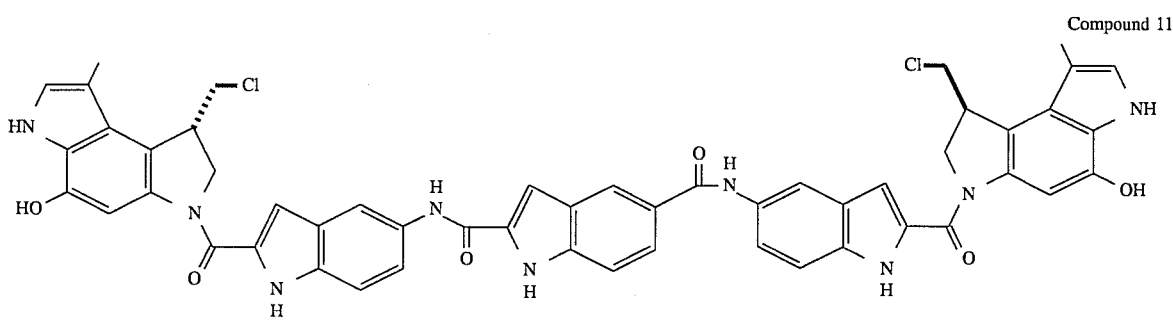
Compound 11
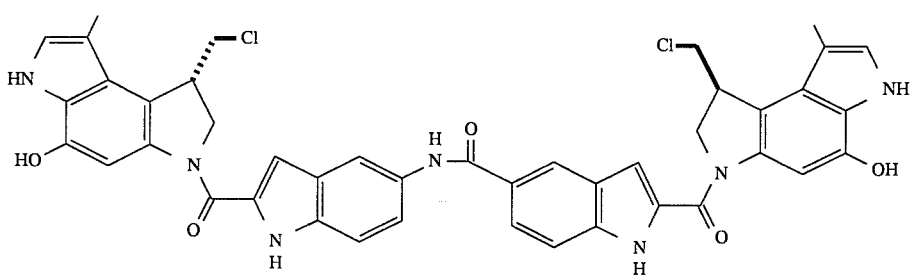
Compound 12
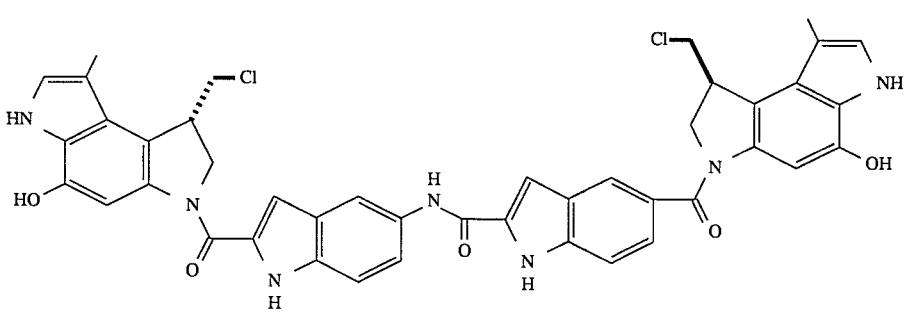
Compound 13

-continued
GENERAL FORMULA CHART

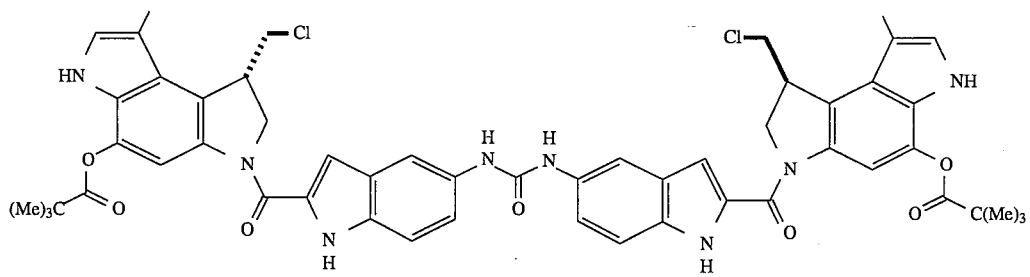
Compound 14

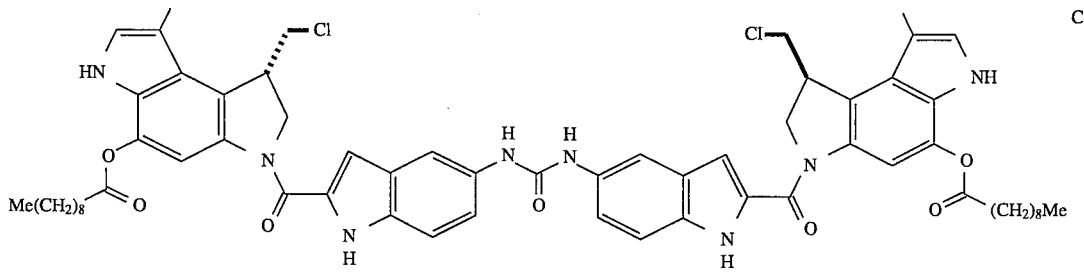
Compound 15

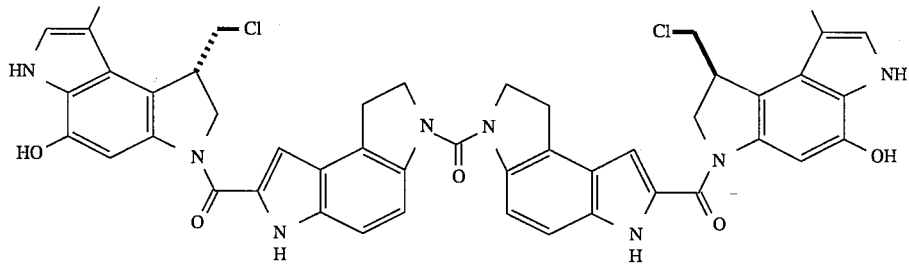
Compound 16

SUPPLEMENTAL FORMULA CHART

-het- is selected from the group consisting of:

a) 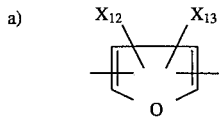

where $X_{12}$ and and $X_{13}$ are the same or different and are H, halogen, $C_1$–$C_5$ alkyl, or $NO_2$;

b) 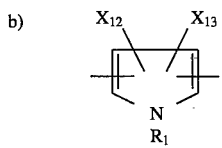

where $X_{12}$ and $X_{13}$ are as defined above and $R_1$ is $C_1$–$C_5$ alkyl;

c) 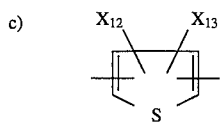

where $X_{12}$ and $X_{13}$ are as defined above;

d) 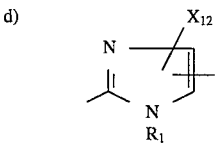

where $X_{12}$ and $R_1$ are as defined above;

e) 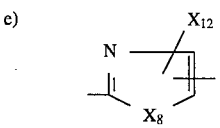

where $X_{12}$ is as defined above and $X_8$ is —O—, —S—, —NH—;

f) 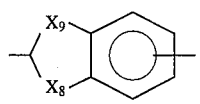

wherein $X_8$ is as defined above and $X_9$ is —CH= or —N=;

g) 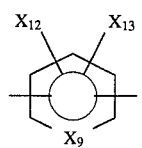

where $X_9$, $X_{12}$ and $X_{13}$ are as defined above;

h) 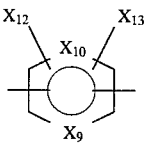

where $X_2$ and $X_{13}$ are as defined above, and when $X_9$ and $X_{10}$ are the same or different, and are selected from —CH= or —N=;

i) 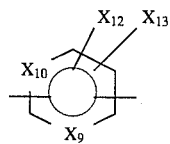

wherein $X_9$, $X_{10}$, $X_{12}$, $X_{13}$ are as defined above;

j) 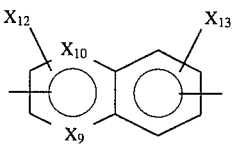

where $X_9$, $X_{10}$, $X_{12}$ and $X_{13}$ are as defined above;

k) 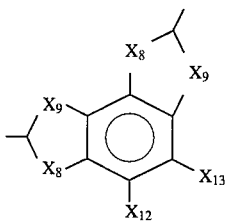

wherein $X_8$, $X_9$, $X_{12}$ and $X_{13}$ are as defined above;

CHART C

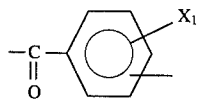 (ii)

where $X_1$ is H, CH$_3$, OH, OCH$_3$, NO$_2$, NH$_2$, (NHNHAc) NHNHC(O)CH$_3$, (NHBz) NHC(O)C$_6$H$_5$, or halogen;

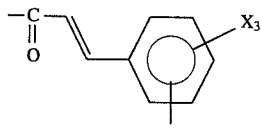 (vi)

where $X_3$ is H, OH or OCH$_3$;

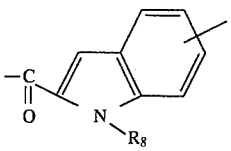 (viii)

where $R_8$ is H, CH$_3$ or C$_2$H$_5$;

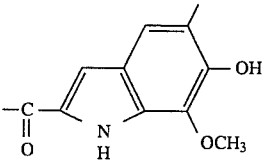 (x)

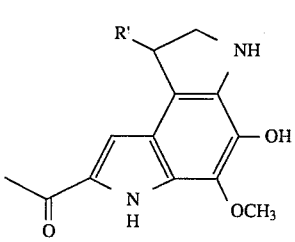 (xi)

wherein R' is H or CH$_3$S—;

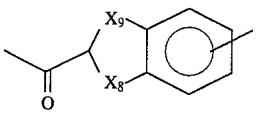 (xvii)

where $X_8$ is —O—, —S—, NH; $X_9$ is —CH= or —N=;

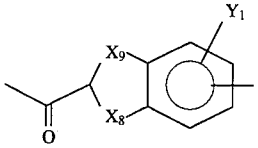 (xviia)

where $X_9$ and $X_8$ have the meanings defined above; and $Y_1$ is H, halo, C$_1$–C$_4$-alkyl, C$_1$–C$_3$-alkoxy, C$_2$–C$_6$-dialkyl amino, nitro, amino-carbon ylalkyl(C$_1$–C$_{10}$), hydroxy, amino (—NH$_2$), —NHCONH$_2$, —NHAc (NHCOCH$_3$) or —NHBz (NHC(O)—C$_6$H$_5$);

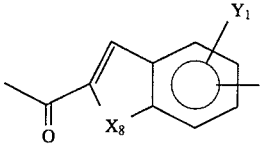 (viib)

where $X_8$ and $Y_1$ have the meanings defined above;

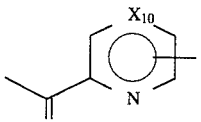 (xix)

where $X_{10}$ is —CH= or —N=;

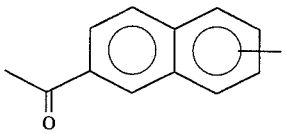 (xx)

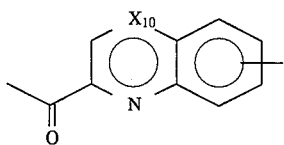 (xxi)

where $X_{10}$ has the meanings defined above; and

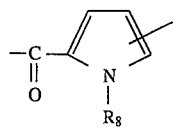 (xxii)

where $R_8$ has the meanings defined above,

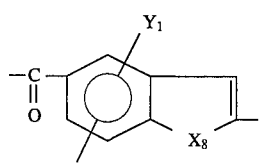 (xxiii)

wherein $Y_1$ and $X_8$ have the meanings defined above;

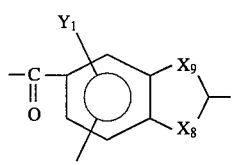 (xxiv)

wherein $Y_1$, $X_8$ and $X_9$ have the meanings defined above;

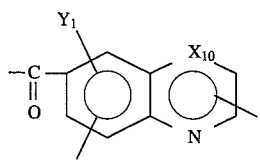 (xxv)

wherein $X_{10}$ is —CH= or —N=, and $Y_1$ have the meanings defined above;

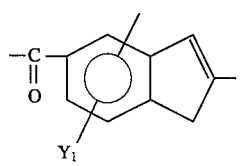 (xxvi)

wherein and $Y_1$ has have the meanings defined above.

TABLE 1

L-1210 Leukemia in vivo
IV drug vs IP tumor dosed on day 1
L1210 In vivo

| Compound # | Dose (μg/kg) | Best T/C[b] |
|---|---|---|
| 14 | 20 | 156 |
| 9 | 50 | 165 |
| 10 | 6 | 213 (1 cure) |
| 11 | 13 | 188 |
| 12 | 2 | 181 |
| 13 | 13 | 188 |
| U-73,975 | 100 | 213 |
| 1 | 15 | 4/6 cures |

TABLE 1-continued

L-1210 Leukemia in vivo
IV drug vs IP tumor dosed on day 1
L1210 In vivo

| Compound # | Dose (μg/kg) | Best T/C[b] |
|---|---|---|
| 3 | 6 | 106 |
| 8 | 50 | 194 |
| 2 | 10 | 169 |
| 6 | 5 | 178 (1 cure) |
| 7 | 1 | 156 |
| 5 | 600 | 156 |
| 4 | 50 | 156 |
| 15 | 13 | 243 (1 cure) |
| 16 | 12 | 243 (1/6 cure) |

[a]Male BDF$_1$ mice
[b]T/C = Treated/Control × 100, where Treated is the median survival time of the treated group and control is the median survival time of the untreated control group. Animals surviving 30 days are considered cured.

TABLE 2

In vitro Biological Data

| Compound # | ID$_{50}$[b] |
|---|---|
| 1 | 0.000001 |
| 3 | 0.000009 |
| 8 | 0.000006 |
| 2 | 0.000001 |
| 6 | 0.000012 |
| 7 | 0.000004 |
| 5 | 0.00001 |
| 4 | 0.000004 |
| 15 | 0.000001 |
| 16 | 0.000002 |

[a]Drugs are tested against L1210 leukemia cells.
[b]The concentration of drug in μg/ml which inhibits cell growth 50% is reported.

TABLE 3

|  |  | U-73-975 | Cpd 1 |
|---|---|---|---|
| L-1210 i.p.[a] i.v. dose on day 1 | OD[b] μg/kg best T/C (cures)[c] | 100 213 | 10–15 (4/6) |
| L-1210 i.p.[a] i.p. dose on days 1, 5, 9 | OD μg/kg T/C (cures) | 20 (4/6) | 4 (3/6) |
| L-1210 sc i.p. dose on day 1 | OD μg/kg best T/C | 100 (4/6) | 10–25 (6/6) |
| B-16 i.p. i.v. dose on day 1 | OD μg/kg T/C | 100 160 | 15 167 |
| Lewis Lung i.v. i.v. dose μg/kg on days 1, 5, 9 | OD T/C | 25 147 | 4 168 |
| NO TUMOR |  | No Delayed Death | No Delayed Death |

[a]i.p. = intraperitoneally and i.v. = intravenously
[b]Od = optimum dose
[c]In these tests, animals which survive 30 days are considered cured

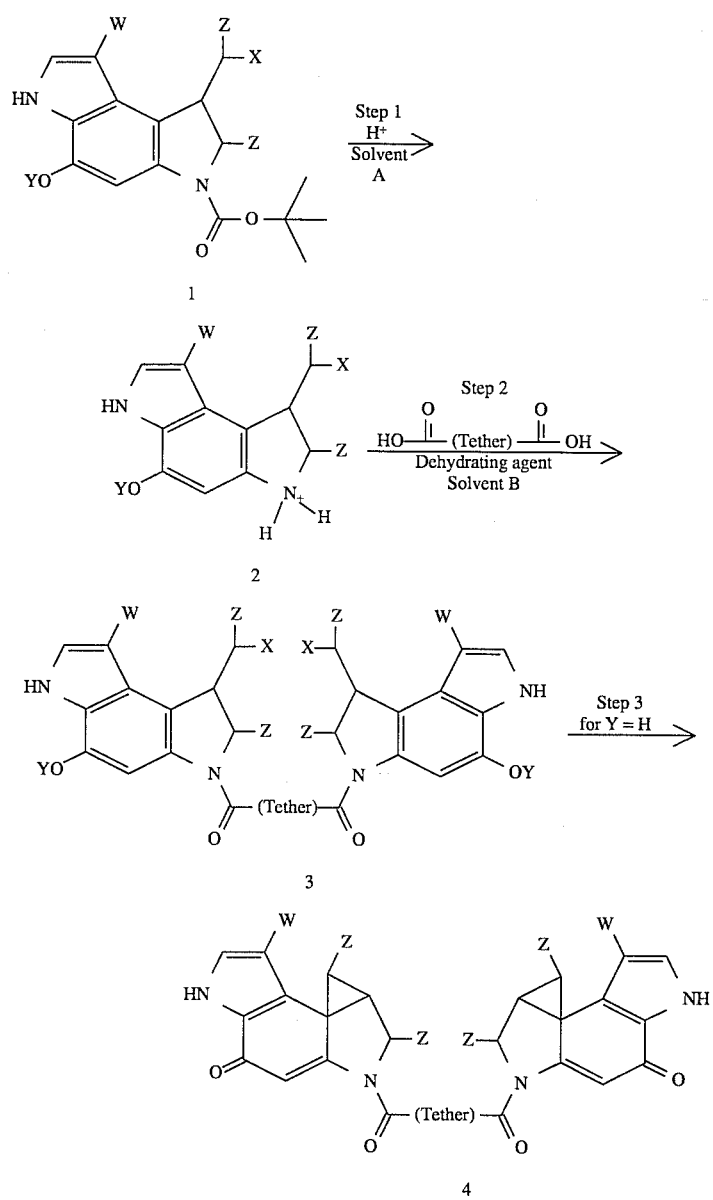
Scheme 1

Scheme 2
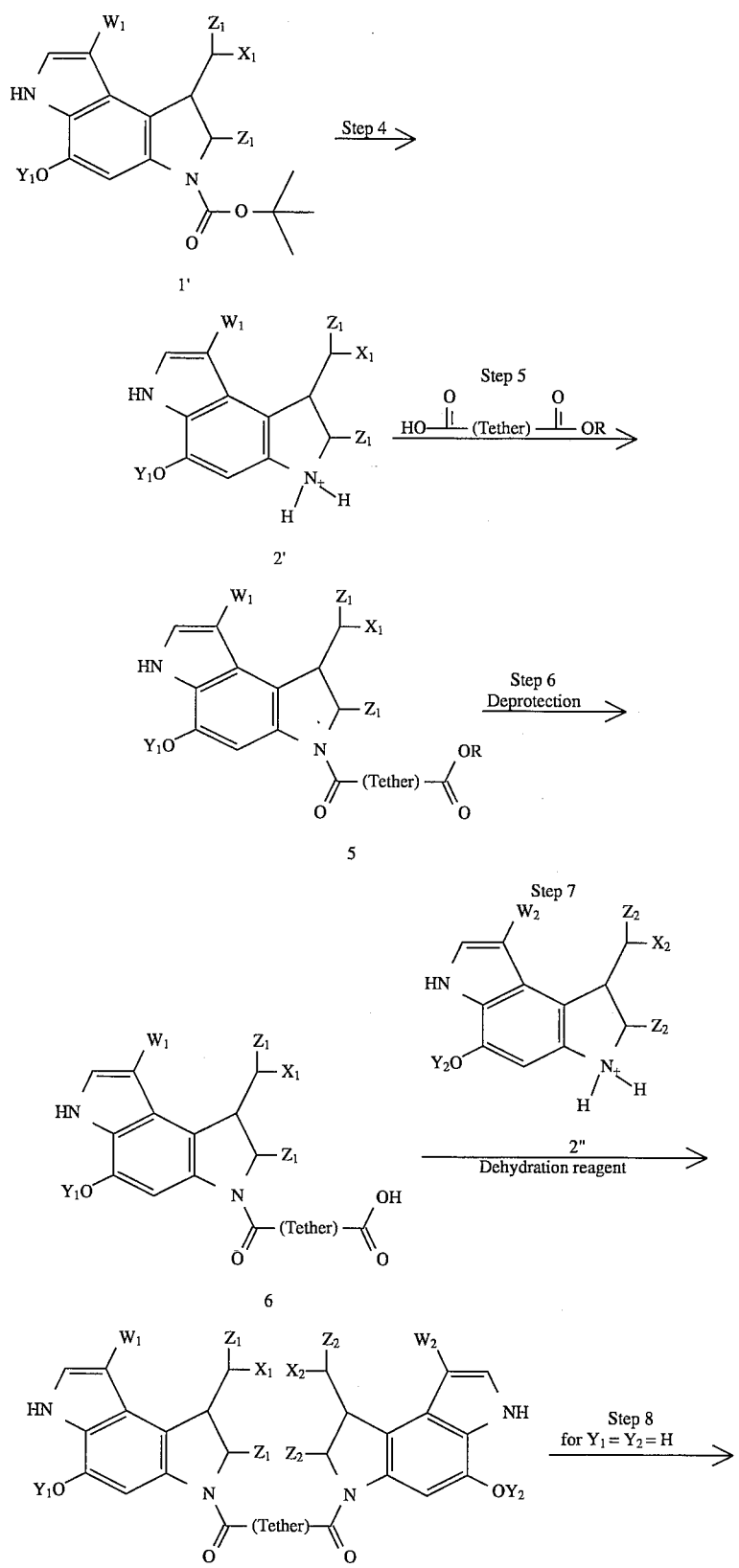

-continued
Scheme 2
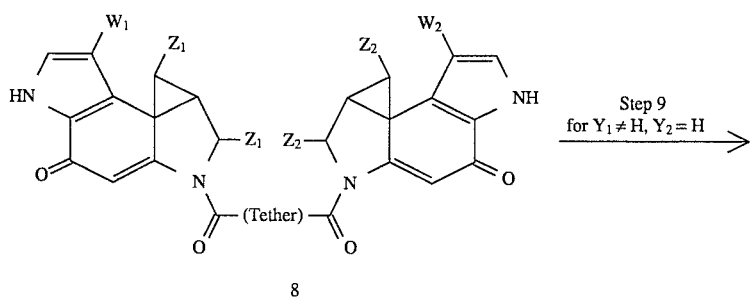
Scheme 2a
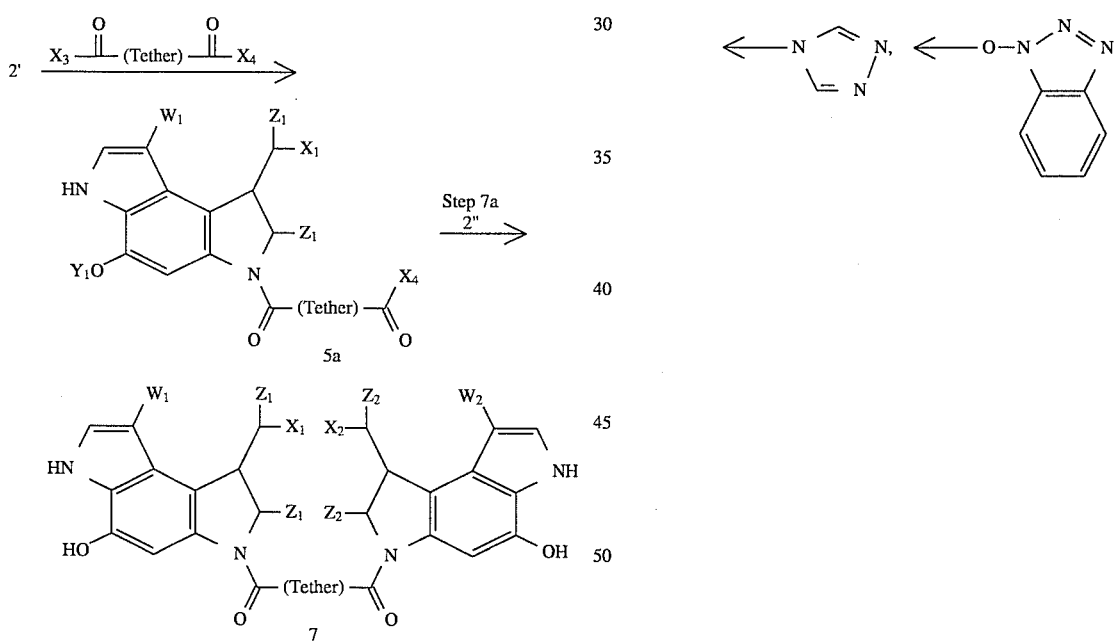
Where $x_3 = x_4$ and are good leaving groups such as:
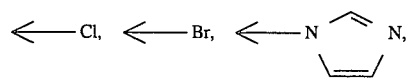

Scheme 3
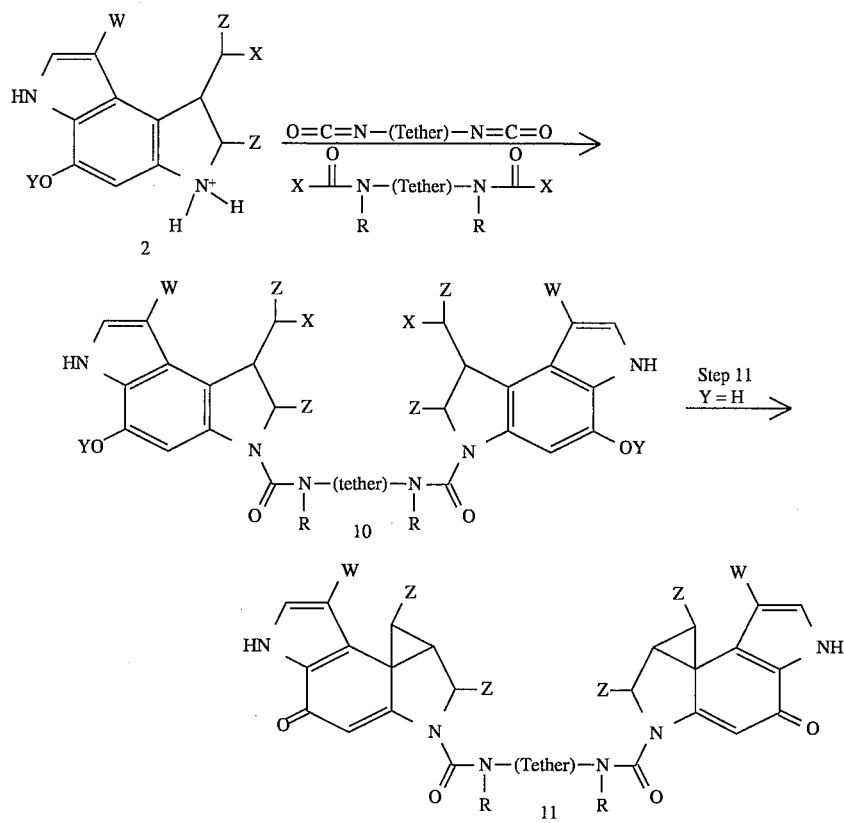

5,541,339
Scheme 4
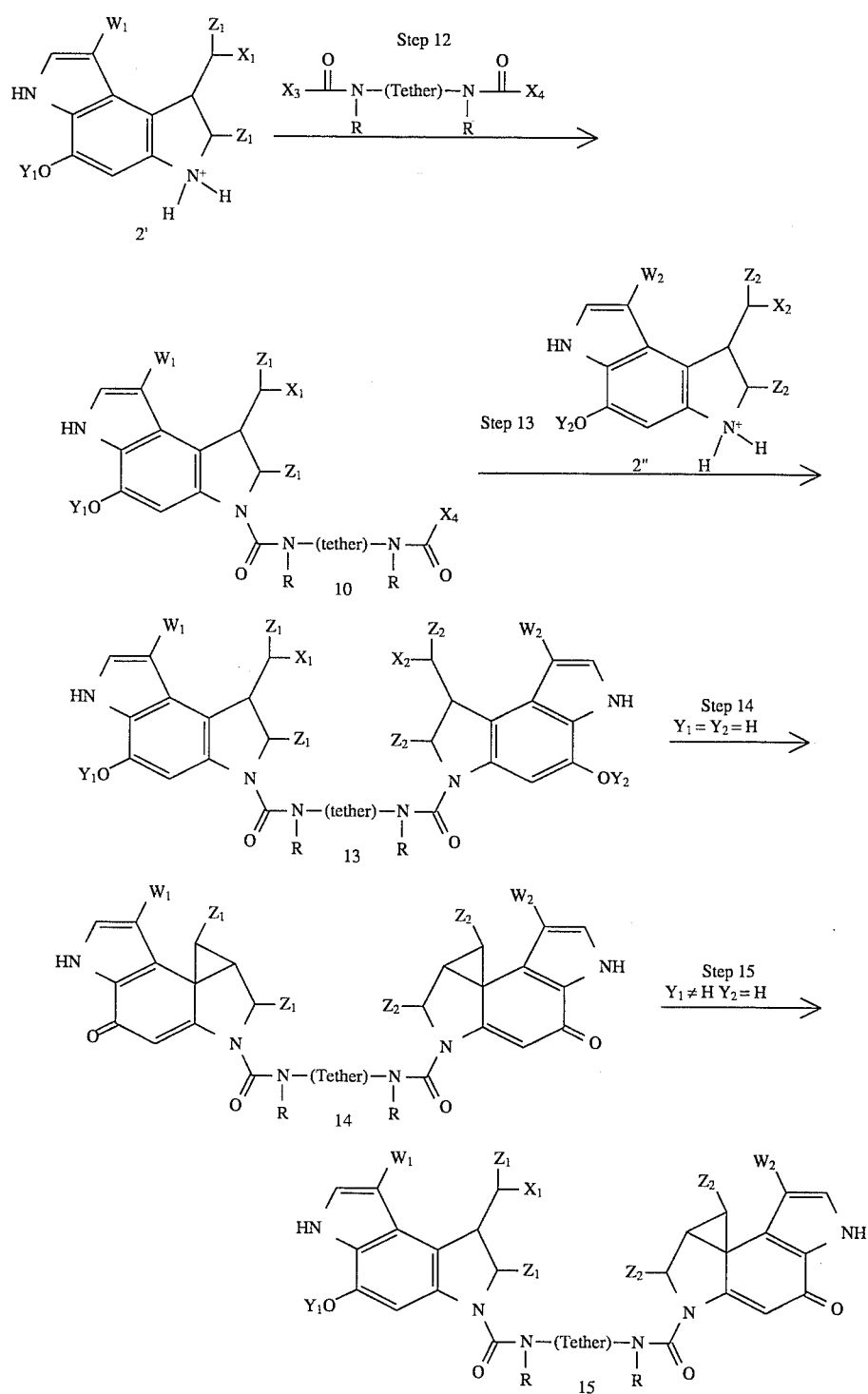

Scheme 5
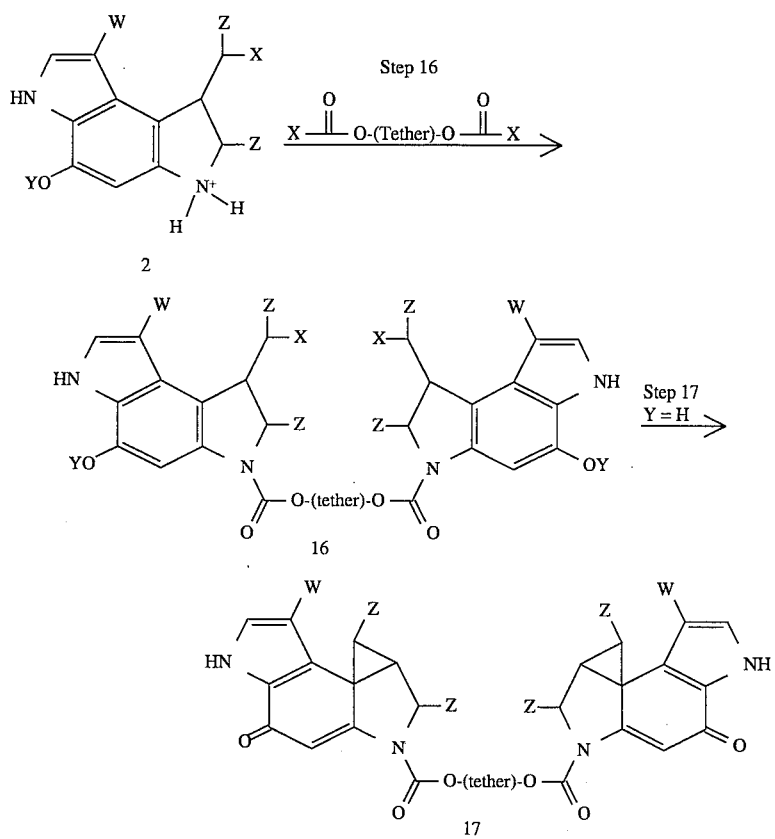
Scheme 6
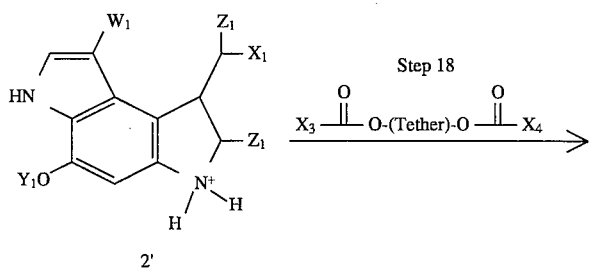

-continued
Scheme 6
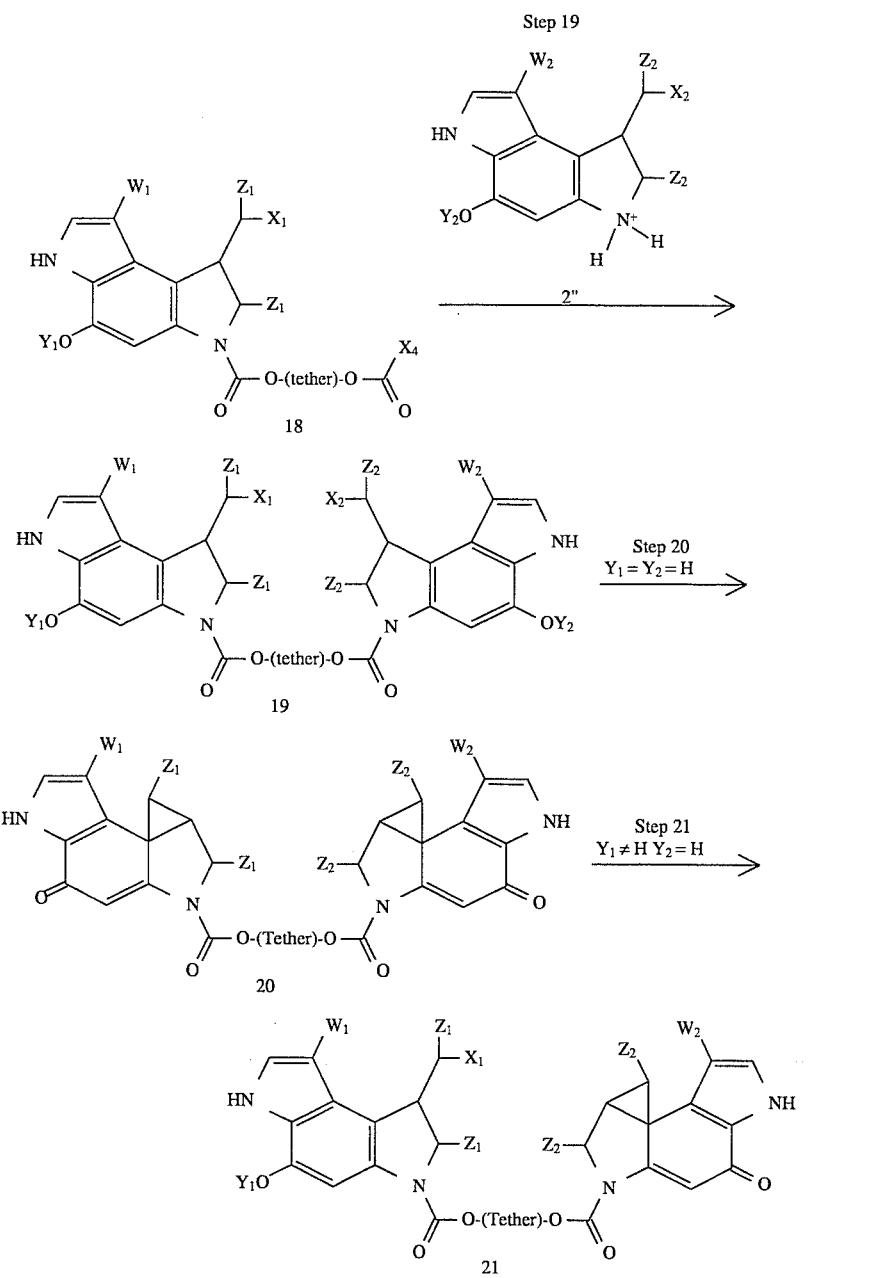
What is claimed is:
1. A compound of formula I
CPI$_1$-R$_5$T-R'$_5$-CPI$_2$
wherein CPI$_1$ and CPI$_2$, being the same or different, are selected from Formula A or B
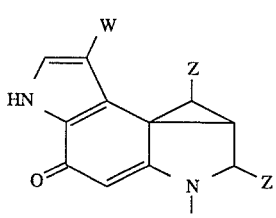
A -continued

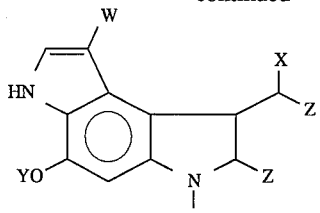
B wherein W is selected from $C_1$–$C_5$ alkyl, phenyl or hydrogen;

wherein X is selected from azido, a halogen atom, cyanate, thiocyanate, isocyanate, thioisocyanate, phosphate diester (—PO(OR)$_2$), phosphonyl (—O—PO$_2$R), thiophosphonyl (—O—PSOR), sulfinyl (—O—SOR) or sulfonyl (—O—SO$_2$R);

wherein Y is selected from hydrogen, —C(O)R, —C(S)R, —C(O)OR$_1$, —S(O)$_2$R$_1$, —C(O)NR$_2$R$_3$, —C(S)NR$_2$R$_3$, or —C(O)NHSO$_2$R$_4$;

wherein Z is selected from the group consisting of $C_1$–$C_5$ alkyl, phenyl or hydrogen;

wherein R is selected from the group consisting of $C_1$–$C_{20}$ alkyl; $C_2$–$C_6$ alkenyl; $C_2$–$C_6$ alkynyl; phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; naphthyl optionally substituted with one or 2 $C_1$–$C_4$ alkyl, $C_1$–$C_3$ alkoxy, halo, trifluromethyl, $C_2$–$C_6$ dialkylamino, $C_1$–$C_3$ alkylthio or nitro;

wherein R$_1$ is selected from $C_1$–$C_{20}$ alkyl or phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro;

wherein R$_2$ and R$_3$, being the same or different, are selected from hydrogen, $C_1$–$C_{20}$ alkyl, or phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; with the proviso that both R$_2$ and R$_3$ can not be phenyl or substituted phenyl;

wherein R$_4$ is selected from $C_1$–$C_{10}$ alkyl; phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; naphthyl optionally substituted with one or 2 $C_1$–$C_4$ alkyl, $C_1$–$C_3$ alkoxy, halo, trifluromethyl, $C_2$–$C_6$ dialkylamino, $C_1$–$C_3$ alkylthio or nitro;

wherein R$_5$ and R'$_5$, being the same or different, are selected from a direct bond or a carbonyl acyl group selected from the group consisting of:

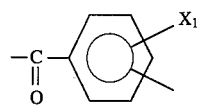
(ii)

where X$_1$ is H, CH$_3$, OH, OCH$_3$, NO$_2$, NH$_2$, (NHNHAc) NHNHC(O)CH$_3$, (NHBz) NHC(O)C$_6$H$_5$, or halogen;

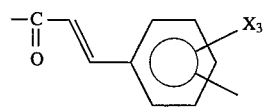
(vi)

where X$_3$ is H, OH or OCH$_3$;

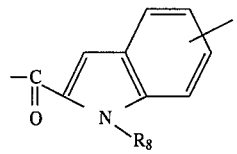
(viii)

where R$_8$ is H, CH$_3$ or C$_2$H$_5$;

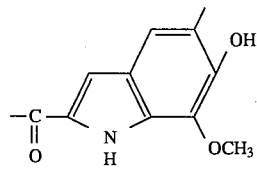
(x)

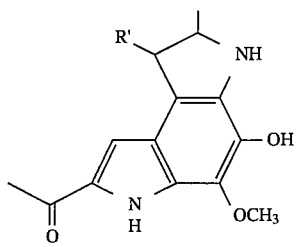
(xi)

wherein R' is H or CH$_3$S—;

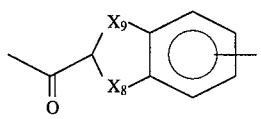
(xvii)

where X$_8$ is —O—, —S—, NH; X$_9$ is —CH= or —N=;

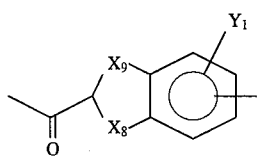
(xviia)

where X$_9$ and X$_8$ have the meanings defined above: and Y$_1$ is H, halo, $C_1$–$C_4$-alkyl, $C_1$–$C_3$-alkoxy, $C_2$–$C_6$-dialkylamino, nitro, amino-carbon ylalkyl($C_1$–$C_{10}$), hydroxy, amino (—NH$_2$), —NHCONH$_2$, —NHAc (NHCOCH$_3$) or —NHBz (NHC(O)—C$_6$H$_5$);

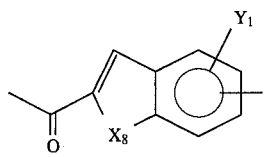
(viib)

where X$_8$ and Y$_1$ have the meanings defined above;

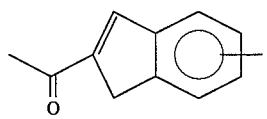
(xviii)

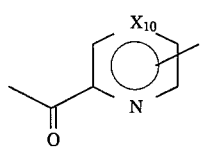
(xix)

where $X_{10}$ is —CH= or —N=;

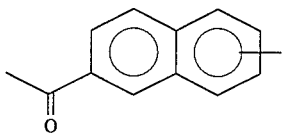 (xx)

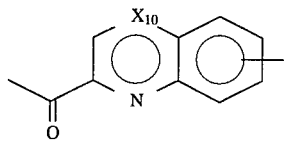 (xxi)

where $X_{10}$ has the meanings defined above; and

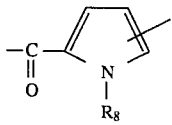 (xxii)

where $R_8$ has the meanings defined above;

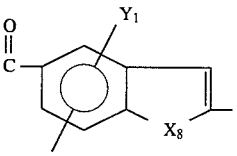 (xxiii)

wherein $Y_1$ and $X_8$ have the meanings defined above;

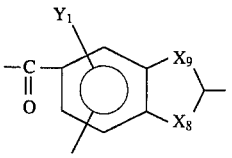 (xxiv)

wherein $Y_1$, $X_8$ and $X_9$ have the meanings defined above;

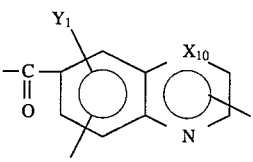 (xxv)

wherein $X_{10}$ is —CH= or —N=, and $Y_1$ have the meanings defined above;

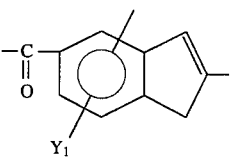 (xxvi)

wherein $Y_1$ has the meanings defined above;
wherein T is a tether linkage selected from the group consisting of:
a) amino carbonyl (—NHC(O)—);
b) carbonylamino (—C(O)NH—);
c) carbonyloxy (—C(O)O—);
d) oxycarbonyl (—OC(O)—);
e) amino-tether-amino of the formula -$NR_{13}$-T'-$NR_{14}$- where $R_{13}$ and $R_{14}$, being the same or different, are hydrogen or $C_1$-$C_8$ alkyl; or when taken together are —(CH$_2$)$_n$— where n is 2 or 3:
where T' is selected from the group consisting of carbonyl (—C(O)—), dicarbonyl (—C(O)C(O)—); (—C(O)(CH$_2$)$_n$C(O)—), where n is 1 to 5, (—C(O)PhC(O)—), where Ph is 1,3- or 1,4- phenylene, or a group of the formula —C(O)-het-C(O)—;
f) —C(O)-het-C(O)—, when $R_5$ and $R'_5$ are both a direct bond, wherein -het- is a fused mono-, di-, or tricyclic heteroaryl of 5 to 12 members, containing one, two, or three heteroatoms selected from the group consisting of oxygen, nitrogen or sulfur, optionally substituted with one or 2 $C_1$-$C_4$ alkyl, $C_1$-$C_3$ alkoxy, halo, $C_1$-$C_3$ alkylthio, trifluoromethyl, $C_2$-$C_6$ dialkylamino, or nitro.

2. A compound according to claim 1 wherein W is methyl.

3. A compound according to claim 1 wherein X is halogen.

4. A compound according to claim 1 wherein Y is hydrogen or selected from the group consisting of —COR, wherein R is selected from $C_1$-$C_{10}$ alkyl.

5. A compound according to claim 1 wherein Z is hydrogen.

6. A compound according to claim 1 wherein T is selected from the the group consisting of an amide (aminocarbonyl); carbonylamino (—C(O)NH—); or an amino-tether-amino of the formula -$NR_{13}$-T'-$NR_{14}$- where $R_{13}$ and $R_{14}$ are hydrogen and where T' is carbonyl (—C(O)—) or is selected from a group of the formula —C(O)-het-C(O)—.

7. A compound according to claim 1 wherein T is selected from the group consisting of an amino-tether-amino of the formula -$NR_{13}$-T'-$NR_{14}$- where $R_{13}$ and $R_{14}$ are hydrogen and where T' is carbonyl (—C(O)—) or is selected from a group of the formula —C(O)-het-C(O)— wherein -het- is a heteroaryl selected from pyrrol-2,5-diyl, fur-2,5-diyl, indol-2,5-diyl, benzofuran-2,5-diyl or 3,6-dihydrobenzo[1,2-b: 4,3-b']dipyrrol-2,7-diyl.

8. A compound according to claim 1 wherein $R_5$ and $R'_5$ are selected from the group consisting of 2-carbonylindole-5-yl, 2-carbonyl-6 -hydroxy-7-methoxyindol-5-yl, 2-carbonyl-1,2,3,6-tetrahydrobenzo[1,2-b: 4,3-b']dipyrrol-7-yl, 2-carbonyl-4-hydroxy-5-methoxy-1,2,3,6-tetrahydrobenzo [1,2-b:4,3-b']dipyrrol-7-yl.

9. A compound according to claim 1 wherein $CPI_1$ and $CPI_2$, being the same or different, are preferably 1-(chloromethyl)-1,6-dihydro-8 -methyl-5-hydroxy-benzo[1,2:4,3-6']dipyrrole-3(2H)-yl and 4,5,8,8 a-tetrahydro-7-methyl-4-oxocyclopropa[c]pyrrolo(3,2-e)indol-2(1H)-yl.

10. A compound according to claim 1 selected from the group consisting of:

[S-(R*,R*)]-6,6'-[carbonylbis(imino-1H-indole-5,2-dicarbonyl)]-bis[8-chloromethyl)-3,6,7,8-tetrahydro-1-methyl-benzo[1,2-b:4,3-b']dipyrrol-4-ol (Compound 1);
[7bR-[2(7'bR*,8'aS*) ,7bR*,8aS*]]-2,2'[carbonylbis(imino-1 H-indole-5,2-dicarbonyl)]bis[1,2,8,8a-tetrahydro-7-methyl-cyclopropa(c)pyrrolo[3,2-e]indol-4(5H)-one (Compound 2);
(R*,S*)-N,N'-bis[2-[[1-(chloromethyl)-1,6-dihydro-5-hydroxy-8 -methylbenzo[1,2-b:4,3-b']dipyrrol-3(2H)-yl] carbonyl]-1H-indol-5-yl]-ethanediamide (Compound 3);
[S-(R*,R*)]-6,6'-(1H -pyrrole-2,5-diyldicarbonyl)bis[8-(chloromethyl)- 3,6,7,8-tertrahydro-1-methyl-benzo[1,2-b:4,3-b'-]dipyrrol-4 -ol (Compound 4):
[S-(R*,R*)]-6,6'-(2,5-furandiyldicarbonyl)bis[8-(chloromethyl)- 3,6,7,8-tetrahydro-1-methyl-benzo[1,2-b:4,3'b] dipyrrol-4-ol (Compound 5);
[S-(R*,R*)-N,N'-bis[2-[[1-(chloromethyl)-1,6-dihydro-5-hydroxy- 8-methylbenzo[1,2-b:4,3-b']dipyrrol-3(2H)-yl] carbonyl]-1H-indol-5-yl]-2,5-furandicarboxamide (Compound 6);

[S-(R*,R*)]-N,N'-bis[2[[1-(chloromethyl)-1,6-dihydro-5-hydroxy-8-methylbenzo[1,2-b:4,3-b']dipyrrol-3(2H)-yl]carbonyl]-1H-indol-5-yl]-1H-pyrrole-2,5-dicarboxamide (Compound 7);

[R-(R*,S*)]-N,N'-bis[2-[[1-(chloromethyl)-1,6-dihydro-5-hydroxy-8-methylbenzo[1,2-b:4,3-b']dipyrrol-3(2H)-yl]carbonyl]-1H-indol-5-yl]-propanediamide (Compound 8);

[S-(R*,R*)]-6,6'-[carbonylbis(imino-1H-indole-5,2-diylcarbonyl)]bis[8-(chloromethyl)-3,6,7,8-tetrahydro-1-methyl-benzo[1,2b:4,3-b']dipyrrol-4-ol diacetate (Compound 9);

[S-(R*,R*)]-6,6'-(1H-indole-2,5-diyldicarbonyl)bis[8-(chloromethyl)-3,6,7,8-tetrahydro-1-methyl-benzo[1,2-b:4,3-b']dipyrrol-4-ol (Compound 10);

[S-(R*,R*)]-N,N'-bis[2-[[1-(chloromethyl)-1,6-dihydro-5-hydroxy-8-methylbenzo[1,2-b:4,3-b']dipyrrol-3(2H)-yl]carbonyl]-1H-indol-5-yl]-1H-indole-2,5-dicarboxamide (Compound 11);

[S-(R*,R*)]-2-[[1-(chloromethyl)-1,6-dihydro-5-hydroxy-8-methyl-benzo[1,2-b:4,3-b']dipyrrol-3(2H)-yl]carbonyl]-N-[3-[[1-(chloromethyl)-1,6-dihydro-5-hydroxy-8-methylbenzo[1,2-b:4,3-b']dipyrrol-3(2H)-yl] carbonyl]-1H-indol-6-yl]-1H-indole-5-carboxamide (Compound 12);

[S-(R*,R*)]-5-[[1-(chloromethyl)-1,6-dihydro-5-hydroxy-8-methylbenzo[1,2-b:4,3-b']dipyrrol-3(2H)-yl]carbonyl)-N-[2-[[1-(chloromethyl)-1,6-dihydro-5-hydroxy-8-methylbenzo[1,2-b:4,3-b']dipyrrol-3(2H)-yl]carbonyl)-1H-indol-5-yl]-1H-indole-2-carboxamide (Compound 13);

[S-(R*,R*)]-carbonylbis[imino-1H-indole-5,2-diylcarbonyl [1-(chloromethyl)-1,6-dihydro-8-methylbenzo[1,2-b:4,3-b']dipyrrole-3,5(2H)-diyl]]ester, 2,2-dimethylpropanoic acid (Compound 14);

[S-(R*,R*)]-carbonylbis[imino-1H-indole-5,2-diylcarbonyl [1-(chloromethyl)-1,6-dihydro-8-methylbenzo[1,2-b:4,3-b']dipyrrole-3,5(2H)-diyl]]ester, decanoic acid (Compound 15);

[S-(R*,R*)]-6,6'-[carbonylbis[(7,8-dihydrobenzo[1,2-b:4,3-b']dipyrrole-6,2(3H)-diyl)carbonyl]]bis[8-(chloromethyl)-3,6,7,8-tetrahydro-1-methyl-benzo[1,2-b:4,3b']dipyrrol-4-ol (Compound 16).

* * * * *